(12) United States Patent
Berthel et al.

(10) Patent No.: US 7,226,915 B2
(45) Date of Patent: Jun. 5, 2007

(54) DIAMINOPYRROLOQUINAZOLINES COMPOUNDS AS PROTEIN TYROSINE PHOSPHATASE INHIBITORS

(75) Inventors: Steven Joseph Berthel, Mendham Township, NJ (US); Kshitij Chhabilbhai Thakkar, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/835,713

(22) Filed: Apr. 30, 2004

(65) Prior Publication Data

US 2004/0229890 A1 Nov. 18, 2004

Related U.S. Application Data

(60) Provisional application No. 60/562,763, filed on Apr. 16, 2004, provisional application No. 60/470,780, filed on May 15, 2003.

(51) Int. Cl.
*A61K 31/519* (2006.01)
*C07D 487/02* (2006.01)
*C07D 209/04* (2006.01)

(52) U.S. Cl. .................. 514/80; 514/267; 514/293; 544/244; 544/250

(58) Field of Classification Search .................. 514/80, 514/293, 267; 544/244, 250
See application file for complete search history.

(56) References Cited

U.S. PATENT DOCUMENTS 4,118,561 A * 10/1978 Ledig .................. 544/250
4,208,520 A * 6/1980 Ledig et al. .................. 544/250
4,233,445 A * 11/1980 Ledig et al. .................. 544/250
4,288,595 A * 9/1981 Ledig et al. .................. 544/250
6,740,657 B2 * 5/2004 Maryanoff et al. .......... 514/267

FOREIGN PATENT DOCUMENTS

| WO | 0 542 497 A1 | 5/1993 |
| WO | WO 99/58522 A1 | 11/1999 |
| WO | WO 02/068423 A1 | 9/2002 |

OTHER PUBLICATIONS

Moeller et al., Current Opinion in Drug Discovery and Development, 3, pp. 527-540 (2000).
Zhang, Zhong-Yin, Current Opinion in Chemical Biology, 5, pp. 416-423 (2001).
Martin et al., Acta Chemica Scandinavica, 47, pp. 221-230 (1993).
Suzuki, Akira, Pure and Appl. Chem., 57, pp. 1749-1758 (1985).
Ansel et al., Pharamaceutical Dosage Forms and Drug Delivery Systems, (6th Ed.) pp. 196 (1995).
Zhang et al., Expert Opin. Investig. Drugs, 12, pp. 223-233 (2003).
Suzuki et al., Synthetic Communications, 11, pp. 513-519 (1981).
Suzuki et al., Chem. Rev., 95, pp. 2457-2483 (1995).
Shieh et al., J. Org. Chem., 57, pp. 379-381 (1992).
Stille, John K., Agnew. Chem. Int. Ed. Engl., 25, pp. 508-524 (1986).
Rob Hooft Van Huijsduijnen et al, (XP-001156666), Drug Discovery Today, vol. 7, No. 19, pp. 1013-1019 (2002).

* cited by examiner

*Primary Examiner*—James O. Wilson
*Assistant Examiner*—Tamthom N. Truong
(74) *Attorney, Agent, or Firm*—George W. Johnston; Dennis P. Tramaloni

(57) ABSTRACT

This invention relates to diaminopyrroloquinazoline compounds which are useful for inhibiting protein tyrosine phosphatases, particularly PTP1B, and are useful for lowering blood glucose concentrations in mammals.

57 Claims, No Drawings

DIAMINOPYRROLOQUINAZOLINES COMPOUNDS AS PROTEIN TYROSINE PHOSPHATASE INHIBITORS

PRIORITY TO PROVISIONAL APPLICATION(S) UNDER 35 U.S.C. §119(e)

This application claims priority under 35 U.S.C. §119(e) of provisional application(s) Ser. No. 60/470,780, filed May 15, 2003 and Ser. No. 60/562,763, filed Apr. 16, 2004.

FIELD OF THE INVENTION

The invention relates to diaminopyrroloquinazolines compounds, useful for inhibiting protein tyrosine phosphatases, particularly PTP1B, and for lowering blood glucose concentrations in mammals.

BACKGROUND OF THE INVENTION

Protein tyrosine phosphatases (PTPases) are key enzymes in processes that regulate cell growth and differentiation. The inhibition of these enzymes can play a role in the modulation of multiple signaling pathways in which tyrosine phosphorylation dephosphorylation plays a role. PTP1B is a particular protein tyrosine phosphatases that is often used as a prototypical member of that class of enzymes.

PTPase inhibitors are recognized as potential therapeutic agents for the treatment of diabetes. See, e.g. Moeller et al., 3(5):527–40, Current Opinion in Drug Discovery and Development, 2000; or Zhang, Zhong-Yin, 5:416–23, Current Opinion in Chemical Biology, 2001. The utility of PTPase inhibitors as therapeutic agents has been a topic of discussion in several review articles, including, or example, Expert Opin Investig Drugs 12(2):223–33, February 2003.

SUMMARY OF THE INVENTION

It has been discovered that compounds of the formula:

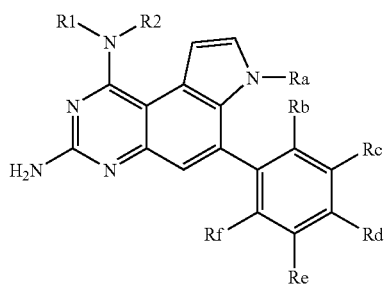

(I)

wherein
R1 is selected from the group consisting of lower alkyl, aryl lower alkyl; acetyl, aryl lower alkoxy lower alkyl, mono- or di-hydroxy substituted lower alkyl;
R2 is selected from the group consisting of hydrogen, lower alkyl, aryl lower alkyl, acetyl, mono- or di-hydroxy substituted lower alkyl and aryl lower alkoxy lower alkyl;
Ra is selected from the group consisting of hydrogen, aryl lower alkyl, lower alkyl, lower alkoxy, mono- or di-hydroxy substituted lower alkyl and

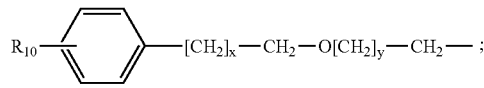

$R_{10}$ is selected from hydrogen and

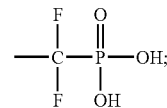

Rb, Rc, Rd, Re and Rf are individually selected from the group consisting of hydrogen, perfluro-lower alkyl, halogen, lower alkyl substituted aryl lower alkyl, lower alkoxy, aryl lower alkoxy and

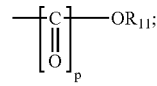

$R_{11}$ is selected from hydrogen, lower alkyl and aryl;
p is an integer from 0 to 1; and
x and y are individually integers from 0 to 4;

or a pharmaceutically acceptable salt thereof, inhibit protein tyrosine phosphatases, particularly PTP1B and are therefore useful for lowering blood glucose concentrations in mammals.

Additionally, it has also been discovered that compounds of the formula:

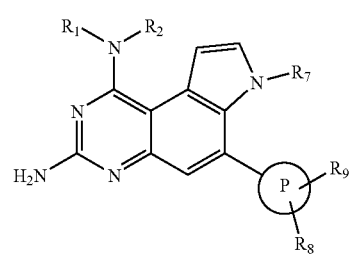

(I-B)

wherein,
Ⓟ is a 5 or 6 membered heteroaromatic ring containing from 1 to 2 hetero atoms selected from the group consisting of oxygen, sulfur and nitrogen;
R1 is selected from the group consisting of lower alkyl, aryl lower alkyl, aryl lower alkoxy lower alkyl, acetyl and mono- or di-hydroxy substituted lower alkyl;
R2 is selected from the group consisting of hydrogen, lower alkyl, acetyl, aryl lower alkyl, aryl lower alkoxy lower alkyl and mono- or di-hydroxy substituted lower alkyl;
$R_7$ is selected from the group consisting of hydrogen, aryl lower alkyl, lower alkyl, lower alkoxy, mono- or di-hydroxy substituted lower alkyl and

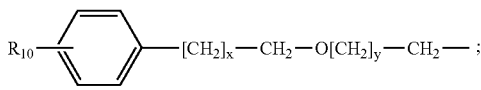

$R_{10}$ is selected from hydrogen and

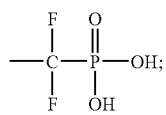

$R_8$ and $R_9$ are individually selected from the group consisting of hydrogen, perfluoro-lower alkyl, halogen, lower alkyl substituted aryl lower alkyl, lower alkyl, aryl lower alkoxy and

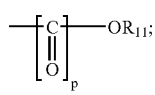

$R_{11}$ is selected from hydrogen, lower alkyl and aryl;
p is an integer from 0 to 1; and x and y are individually integers from 0 to 4 inhibit protein tyrosine phosphatases, particularly PTP1B and are therefore useful for lowering blood glucose concentrations in mammals.

DETAILED DESCRIPTION OF THE INVENTION

The present invention comprises compounds of formula I:

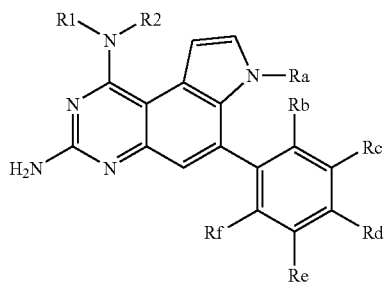

(I)

wherein
R1 is selected from the group consisting of lower alkyl, aryl lower alkyl; acetyl, aryl lower alkoxy lower alkyl and mono- or di-hydroxy substituted lower alkyl;
R2 is selected from the group consisting of hydrogen, lower alkyl, aryl lower alkyl, acetyl, mono- or di-hydroxy substituted lower alkyl, and aryl lower alkoxy lower alkyl;
Ra is selected from the group consisting of hydrogen, aryl lower alkyl, lower alkyl, lower alkoxy, mono- or di-hydroxy substituted lower alkyl and

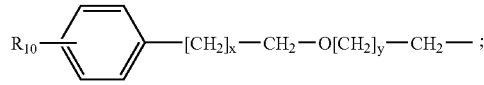

$R_{10}$ is selected from hydrogen and

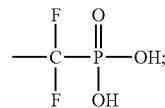

Rb, Rc, Rd, Re and Rf are individually selected from the group consisting of hydrogen, perfluro-lower alkyl, halogen, lower alkyl substituted aryl lower alkyl, lower alkoxy, aryl lower alkoxy and

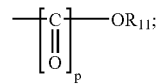

$R_{11}$ is selected from hydrogen, lower alkyl and aryl;
p is an integer from 0 to 1; and
x and y are individually integers from 0 to 4,
or a pharmaceutically acceptable salt thereof,
inhibit protein tyrosine phosphatases, particularly PTP1B and are therefore useful for lowering blood glucose concentrations in mammals.

In a preferred embodiment of formula I of this invention,
R1 is selected from the group consisting of methyl, ethyl, benzyl, acetyl, 2,3-dihydroxypropyl, 3-hydroxypropyl and 2-benzyloxyethyl;
R2 is selected from the group consisting of hydrogen, methyl, ethyl, benzyl, and acetyl;
Ra is selected from the group consisting of hydrogen, methyl, hydroxyethyl, 2-benzyloxy-ethyl and 2-[4-difluorophosphono-methyl]-benzyloxy]-ethyl;
Rb is selected from the group consisting of hydrogen, methyl, methoxy, phenoxy and trifluoromethyl;
Rc and Rd are each independently selected from hydrogen and trifluoromethyl;
Re is selected from the group consisting of hydrogen, chlorine and trifluoromethyl; and
Rf is selected from hydrogen and methyl, or a pharmaceutically acceptable salt thereof.

A preferred embodiment of the compounds of formula I comprises compounds of the formula:

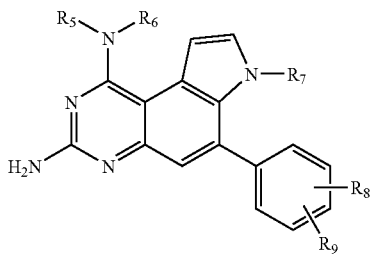

I-A wherein
$R_5$ is selected from the group consisting of hydrogen, lower alkyl, aryl lower alkyl, mono- or di-hydroxy substituted lower alkyl, and aryl lower alkoxy loweralkyl;
$R_6$ is selected from the group consisting of lower alkyl, aryl lower alkyl, mono- or di-hydroxy substituted lower alkyl, and aryl lower alkoxy lower alkyl;
$R_7$ is selected from the group consisting of hydrogen, lower alkyl and mono- or di-hydroxy substituted lower alkyl, or

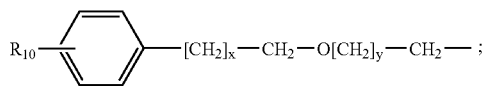

$R_{10}$ is selected from hydrogen and

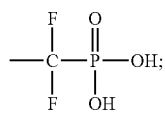

$R_8$ and $R_9$ are individually selected from the group consisting of hydrogen, perfluoro-lower alkyl, halogen, lower alkyl substituted aryl lower alkyl, lower alkyl, aryl lower alkoxy and

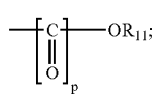

$R_{11}$ is selected from hydrogen, aryl and lower alkyl;
p is an integer from 0 to 1; and
x and y are individually integers from 0 to 4
or a pharmaceutically acceptable salt thereof.

In another embodiment of this invention, compound of the formula:

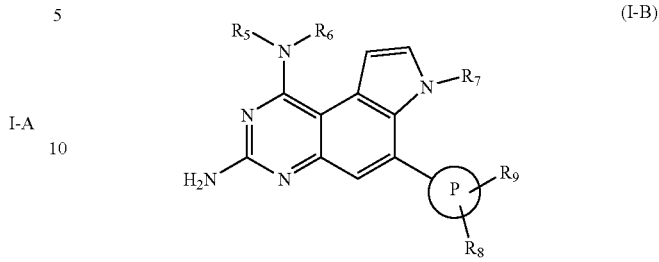

(I-B)

wherein,
(P) is a 5 or 6 membered heteroaromatic ring containing from 1 to 2 hetero atoms selected from the group consisting of oxygen, sulfur and nitrogen;
$R_5$ and $R_6$ are as above;
$R_7$ is selected from the group consisting of hydrogen, aryl lower alkyl, lower alkyl, lower alkoxy, mono- or di-hydroxy substituted lower alkyl and

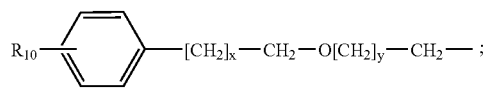

$R_{10}$ is selected from hydrogen and

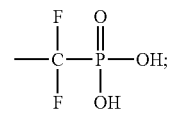

$R_8$ and $R_9$ are individually selected from the group consisting of hydrogen, perfluoro-lower alkyl, halogen, lower alkyl substituted aryl lower alkyl, lower alkyl, aryl lower alkoxy and

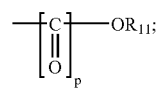

$R_{11}$ is selected from hydrogen, lower alkyl and aryl;
p is an integer from 0 to 1; and
x and y are individually integers from 0 to 4
or a pharmaceutically acceptable salt thereof,
inhibit protein tyrosine phosphatases, particularly PTP1B and are therefore useful for lowering blood glucose concentrations in mammals.

As used in the specification, the term "lower alkyl", alone or in combination, means a straight-chain or branched-chain alkyl group containing from one to six carbon atoms, such as methyl, ethyl, n-propyl, isopropyl, n-butyl, sec-butyl, isobutyl, tert-butyl, n-pentyl, n-hexyl and the like. Examples of substituted lower alkyl groups include 2,3-dihydropropyl and 3-hydroxypropyl.

The term "lower alkoxy" means a straight-chain or branched-chain alkoxy group containing from one to six carbon atoms, such as methoxy, ethoxy, n-propoxy, isopropoxy, n-butoxy, tert-butoxy and the like.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, etc.

The term "heteroaromatic ring" means a mono-cyclic aromatic ring containing one or more hetero atoms in the ring system such as nitrogen atom, oxygen atom and sulphur atom within the ring. Examples of "heteroaryl group" are pyridyl group, thienyl group, pyrimidinyl group, quinolyl group, isoquinolyl group, isoxazolyl group, indolinyl group and furyl group.

The term "aryl" means a mono-aromatic group, such as aryl or naphthyl, which is unsubstituted or substituted by conventional substitutent groups. Preferred substituents are lower alkyl, lower alkoxy, hydroxy lower alkyl, hydroxy, hydroxyalkoxy, halogen, lower alkylthio, lower alkylsulfinyl, lower alkylsulfonyl, cyano, nitro, perfluoroalkyl, alkanyoyl, aroyl, aryl alkynyl, lower alkynyl and lower alkanoylamino. Also preferred substituents are lower alkyl, lower alkoxy, hydroxy, halogen, cyano and perfluoro lower alkyl. Examples of aryl groups that may be used in accordance with this invention are phenyl, p-methoxyphenyl, p-chlorophenyl, m-hydroxy phenyl, m-methylthiophenyl, benzyloxyethyl and the like.

The term "aryl lower alkyl" or "lower alkyl-aryl" means a lower alkyl group in which one or more hydrogen atoms is/are replaced by an aryl group. Any conventional lower alkyl-aryl may be used in accordance with this invention, such as benzyl and the like.

The term "aryl lower alkoxy" or "lower alkoxy-aryl" means a lower alkoxy group in which one or more hydrogen atoms is/are replaced by an aryl group. Any conventional lower alkoxy-aryl may be used in accordance with this invention, such as benzyloxy.

The term "aryl lower alkoxy lower alkyl" means a lower alkyl group substituted on the opposite side of the oxygen atom of an aryl lower alkoxy group. Specifically, aryl lower alkoxy lower alkyl can be represented by aryl-$(CH2)_m$—O—$(CH2)_n$, where m and n are individually integers between 0 to 4.

The term "pharmaceutically acceptable salts" refers to conventional acid-addition salts or base-addition salts that retain the biological effectiveness and properties of the compounds of formulas I, I-A and I-B, and are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., Pharmaceutical Dosage Forms and Drug Delivery Systems (6th Ed. 1995) at pp. 196 and 1456–1457

In particular, the more preferred compound of formulas I and II in this invention includes 7,N1-Dimethyl-6-(2-trifluoromethyl-phenyl)-7H-pyrrolo[3,2-f]quinazoline-1,3-diamine trifluoroacetic acid salt;
6-Furan-2-yl-7,N1-dimethyl-7H-pyrrolo[3,2-f]quinazoline-1,3-diamine trifluoroacetic acid salt;
6-(2,6-Dimethyl-phenyl)-7,N1-dimethyl-7H-pyrrolo[3,2-f]quinazoline-1,3-diamine trifluoroacetic acid salt;
7,N1-Dimethyl-6-thiophen-2-yl-7H-pyrrolo[3,2-f]quinazoline-1,3-diamine trifluoro-acetic acid salt;
7-Ethyl-N1-methyl-6-thiophen-2-yl-7H-pyrrolo[3,2-f]quinazoline-1,3-diamine trifluoro-acetic acid salt;
6-(5-Methoxy-thiophen-2-yl)-7,N1-dimethyl-7H-pyrrolo[3,2-f]quinazoline-1,3-diamine; and
6-(4-Methoxy-thiophen-2-yl)-7,N1-dimethyl-7H-pyrrolo[3,2-f]quinazoline-1,3-diamine.

In the preferred compounds of formula I-A, there are several preferred embodiments of these compounds. In accordance with a first embodiment, R is hydrogen or lower alkyl, $R_6$ is lower alkyl and $R_8$ and $R_9$ are perfluoroloweralkyl, preferably trifluoromethyl, with at least one of $R_8$ and $R_9$ being perfluoroloweralkyl. In accordance with this first embodiment of the compound of formula I-A, $R_7$ can be hydrogen, lower alkyl or mono- or di-hydroxy substituted lower alkyl and $R_8$ and $R_9$ being perfluoroloweralkyl such as trifluoromethyl and the other being hydrogen or perfluoroloweralkyl.

In accordance with another embodiment of the compound of formula I-A, $R_7$ can be

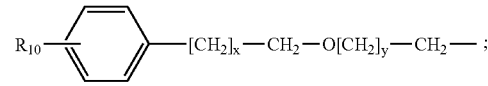

wherein $R_{10}$, x and y are as above. In accordance with this embodiment, $R_5$ can be hydrogen or lower alkyl and $R_6$ can be lower alkyl. In addition, in an especially preferred class of this embodiment, $R_8$ and $R_9$ can be perfluoroloweralkyl or hydrogen with at least one of $R_8$ and $R_9$ being perfluoroloweralkyl.

In accordance with still another embodiment of the compound of formula I-A, one of $R_8$ and $R_9$ is lower alkyl, with both of $R_8$ and $R_9$ being lower alkyl being especially preferred. On the other hand, in this embodiment, R8, and $R_9$ can be both hydrogen or one of $R_8$ and $R_9$ can be hydrogen and the other lower alkyl. In yet another embodiment of the compound of formula I-A, one of $R_8$ and $R_9$ is lower alkoxy or a substituent of the formula:

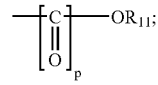

wherein $R_{11}$ and p are as above. In this embodiment, compounds where one of $R_5$ and $R_6$ are lower alkyl are especially preferred. In addition, in this especially preferred embodiment, compounds where $R_7$ are lower alkyl are preferred.

With respect to the compound of formula I-B there are many embodiments in accordance with the inventions embraced within this formula. The heteroaromatic ring in accordance with this invention preferably contains 5 or 6 members in the ring. Among these are compounds of formula I-B where the heteroaromatic ring formed within this compound contains a sulfur hetero atom as the only heteroaromatic atom in this ring, such as thiophene rings. Among the compounds containing a thiophene ring are those compounds where $R_8$ and $R_9$ are hydrogen or lower alkyl, $R_5$ is hydrogen, lower alkyl or mono- or di-hydroxy substituted lower alkyl and $R_6$ is lower alkyl or mono- or di-hydroxy substituted lower alkyl. In accordance with the embodiment of the compounds where the heteroaromatic ring is a thiophene ring, among the preferred compounds are those where $R_8$ and $R_9$ are independently hydrogen, lower alkoxy or aryl lower alkoxy with at least one of $R_8$ and $R_9$ being other than hydrogen. In this preferred embodiment, $R_5$ is hydrogen or lower alkyl or mono- or di-hydroxy substituted lower alkyl and $R_6$ is lower alkyl or mono- or di-hydroxy substituted lower alkyl.

In accordance with another embodiment of the compounds of formula I-B, the aromatic ring is 5 or 6 membered heteroaromatic ring containing an oxygen atom as the only hetero atom such as a furanyl ring. In this embodiment, one preferred class of compounds is those where $R_5$ is hydrogen or lower alkyl and $R_6$ is lower alkyl. Another embodiment of the compounds of formula I-B are those compounds wherein the heteroaromatic ring is a 5 or 6 membered heteroaromatic ring containing a nitrogen atom as the only heteroaromatic ring. In accordance with this embodiment, compounds where one of the $R_8$ and $R_9$ substituents are hydrogen and the other is hydrogen, lower alkyl or a substituent of the formula

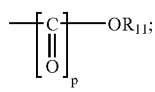

where $R_{11}$ and p are as above. In accordance with this embodiment, compounds where p is 1 is a preferred embodiment, $R_{11}$ is aryl or lower alkyl and $R_5$ and $R_6$ are lower alkyl.

In accordance with another embodiment of the compound of formula I-B, ⓟ can be a heteroaromatic ring containing 5 or 6 members and two hetero atoms such as nitrogen, oxygen or sulfur. In this embodiment, $R_8$ and $R_9$ can be lower alkyl, hydrogen or alkoxy.

This invention is also directed to a pharmaceutical composition comprising one or more compounds of formulas I-A, I-B and I-C.

Moreover, this invention is directed to a method of treating a disease based on high blood glucose concentration comprising administering to a patient in need of such treatment a therapeutically effective amount of at least one compound of the formulas I, I-A, I-B and I-C.

The compounds of the invention can exist as stereoisomers and diastereomers, all of which are encompassed within the scope of the present invention. The compounds of the invention inhibit PTP1B in vitro and have been shown to lower blood glucose levels in vivo. Thus, the compounds of the present invention would be useful for the treatment of diabetes.

The compounds of the invention can be administered orally, rectally, or parentally, e.g., intravenously, intramuscularly, subcutaneously, intrathecally or transdermally; or sublingually, or as opthalmalogical preparations. Capsules, tablets, suspensions or solutions for oral administration, suppositories, injection solutions, eye drops, salves or spray solutions are examples of administration forms.

Intravenous, intramuscular, oral or inhalation administration are preferred forms of use. The dosages in which the compounds of the invention are administered in effective amount depend on the nature of the specific active ingredient, the age and requirements of the patient and the mode of administration. Dosages may be determined by any conventional means, e.g., by dose-limiting clinical trials. In general, dosages of about 0.1 to 100 mg/kg body weight per day are preferred, with dosages of 1–25 mg/kg per day being particularly preferred.

The invention further comprises pharmaceutical compositions that contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present. The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

Oral unit dosage forms, such as tablets and capsules, preferably contain from 25 mg to 1000 mg of a compound of this invention. The compounds of the invention may be prepared by conventional means.

In accordance with this invention, the compounds herein as well as their pharmaceutically acceptable salts are useful in the control or prevention of illnesses associated with high blood glucose concentration. A preferred indication associated with the present invention is that associated with diabetes.

The dosage can vary within wide limits and will, of course, have to be adjusted to the individual requirements in each particular case. In the case of oral administration, the dosage for adults may vary from about 0.01 mg to about 1000 mg per day of a compound of formulas I or II, or of the corresponding amount of a pharmaceutically acceptable salt thereof. The daily dosage may be administered as single dose or in divided doses, and in addition, the upper limit can also be exceeded when this is found to be indicated.

A particular method for preparing the compounds of this invention is described in the following schemes.

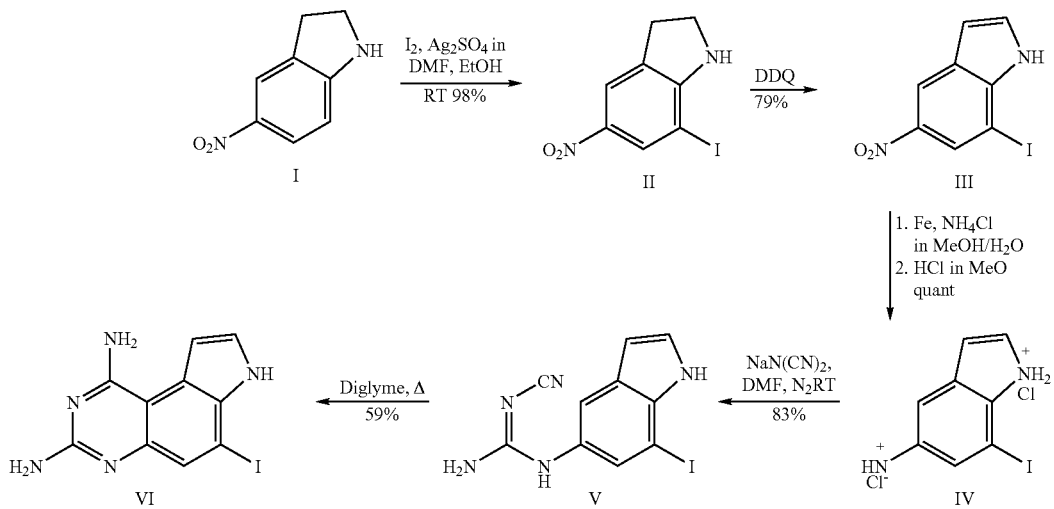
Scheme 2 below provides a general synthesis step, and the examples provide a detailed description of the schematic methods.
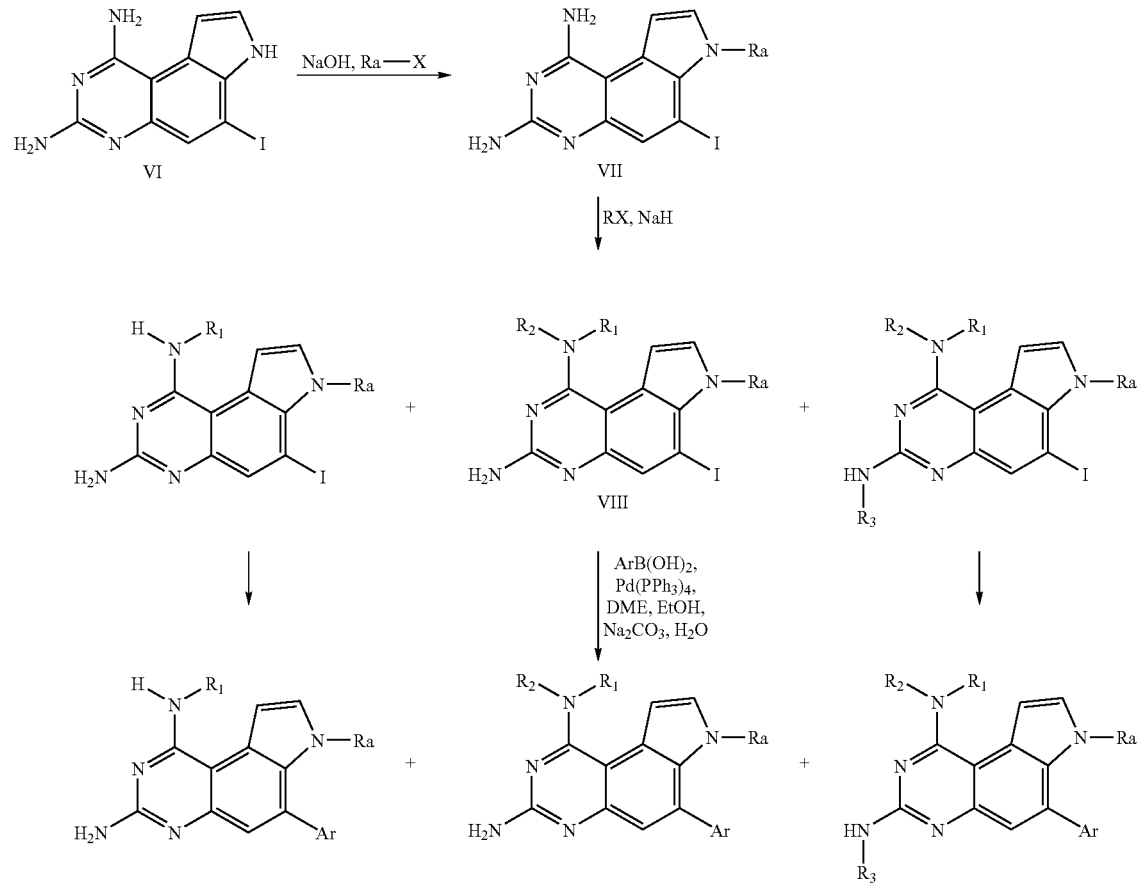

Compound II: A mixture of silver sulfate (100 g, 0.32 mol) and iodine (82 g, 0.32 mol) in N,N-dimethylformamide (700 mL) and ethanol (1400 mL) was treated with 5-nitro-2,3-dihydro-1H-indole I (48 g, 0.29 mol). The resulting mixture was stirred at 25° C. for 1.5 h, filtered and the filter pad washed with ethyl acetate. The filtrate was concentrated in vacuo to a volume of approximately 500 mL. This solution was treated with a 1.0 N aqueous sodium thiosulfate solution (100 mL) and a saturated aqueous sodium chloride solution (400 mL). The resulting precipitate was collected by filtration, washed with water and petroleum ether, and dried in vacuo to afford 7-iodo-5-nitro-2,3-dihydro-1H-indole II (83.9 g, 98.9%) as a white solid: $^1$H NMR (DMSO-$d_6$, 300 MHz) δ 8.18 (d, J=2.20 Hz, 1H), 7.80 (d, J=1.46 Hz, 1H), 7.03 (broad s, 1H), 3.65 (t, J=8.97 Hz, 2H), 3.17 (t, J=8.60 Hz, 2H).

Compound III: A solution of 7-iodo-5-nitro-2,3-dihydro-1H-indole II (15 g, 51.7 mmol) in ethanol (1200 mL) and isopropanol (20 mL) at 25° C. was treated with 2,3-dichloro-5,6-dicyano-1,4-benzoquinone (13.6 g, 59.9 mmol). The resulting solution was warmed to 65° C. and air was bubbled through for 1 h. An additional 0.57 equivalents of 2,3-dichloro-5,6-dicyano-1,4-benzoquinone (6.8 g, 29.9 mmol) was added and the reaction was stirred at 65° C. for another 2 h before being concentrated in vacuo. Flash chromatography (Merck Silica gel 60, 230–400 mesh, 90/10 toluene/ethyl acetate) afforded 7-iodo-5-nitro-1H-indole III (13.07 g, 79%) as a yellow solid: $^1$H NMR (DMSO-$d_6$, 300 MHz) δ 11.82 (broad s, 1H), 8.59 (d, J=1.83 Hz, 1H), 8.30 (d, J=1.83 Hz, 1H), 7.61 (t, J=2.93 Hz, 1H), 6.90 (dd, $J_1$=1.83 Hz, $J_2$=3.30 Hz, 1H).

Compound IV: A solution of 7-iodo-5-nitro-1H-indole III (20 g, 69.4 mmol) in methanol (650 mL) at 25° C. was treated with a solution of ammonium chloride (26.1 g, 485.8 mmol) in water (550 mL) and iron powder (13.6 g, 242.9 mmol). The mixture was heated to 100° C. under a nitrogen atmosphere for 5 h. The resulting mixture was filtered through a pad of celite and the celite pad washed with hot methanol. The filtrate was concentrated in vacuo and the residue was partitioned between methylene chloride and water and separated. The pH of the aqueous layer was adjusted to pH=10 with ammonium hydroxide and extracted with methylene chloride. The combined organic layers were dried over sodium sulfate, filtered, and concentrated in vacuo to a volume of 250 mL. This solution was treated with a 4.0 M aqueous hydrochloric acid solution in dioxane and stirred at 25° C. for 2 h. The precipitate was collected by filtration and washed with methylene chloride and petroleum ether to afford 7-iodo-1H-indol-5-ylamine hydrochloride IV (24.7 g, quant.) as a gray solid: $^1$H NMR (DMSO-$d_6$, 300 MHz) δ 11.34 (broad s, 1H), 9.93 (broad s, 2H), 7.56 (d, J=1.46 Hz, 1H), 7.48 (t, J=2.74 Hz, 1H), 7.44 (d, J=1.83 Hz, 1H), 6.68 (dd, $J_1$=1.83 Hz, $J_2$=2.93 Hz, 1H).

Compound V: A solution of 7-iodo-1H-indol-5-ylamine hydrochloride IV (24.6 g, 83.7 mmol) in N,N-dimethylformamide (400 mL) at 25° C. was treated with sodium dicyanamide (18.6 g, 209 mmol). The reaction mixture was warmed to 50° C. for 2 h, concentrated in vacuo, and the residue treated with water (500 mL). The resulting mixture was allowed to stand at 25° C. for 2.5 h during which time a yellow precipitate formed. The precipitate was collected by filtration and washed with water to afford N"-cyano-N-(7-iodo-1H-indol-5-yl)guanidine V (22.59 g, 83%) as a light yellow solid: $^1$H NMR (DMSO-$d_6$, 300 MHz) δ 11.02 (broad s, 1H), 8.89 (broad s, 1H), 7.46 (d, J=1.83 Hz, 1H), 7.37 (d, J=1.83 Hz, 1H), 7.35 (t, J=2.56 Hz, 1H), 6.85 (broad s, 2H), 6.56 (dd, $J_1$=1.83 Hz, $J_2$=3.10 Hz, 1H).

Compound VI: A solution of N"-cyano-N-(7-iodo-1H-indol-5-yl)guanidine V (6.08 g, 18.7 mmol) in 2-methoxyethyl ether (50 mL) was heated to 175° C. for 32.5 h. The reaction mixture was cooled to 25° C., the resulting solids removed by filtration and washed with methanol. The filtrate was concentrated in vacuo to give a brown oil. The residue was dissolved in methanol and then absorbed onto Merck Silica gel 60, 230–400 mesh (25 g). Flash chromatography (Merck Silica gel 60, 230–400 mesh, 90/10/1 methylene chloride/methanol/ammonium hydroxide) afforded 6-iodo-7H-pyrrolo[3,2-f]quinazoline-1,3-diamine VI (3.61 g, 59%) as a brown solid: $^1$H NMR (DMSO-$d_6$, 300 MHz) δ 11.36 (broad s, 1H), 7.45 (broad s, 1H), 7.43 (t, J=2.93 Hz, 1H), 7.20 (s, 1H), 6.74 (broad s, 2H), 5.78 (broad s, 2H).

Compound VII: Typical condition used to carry out the alkylation of derivatives VI with a variety of halides (e.g., RaBr or RaI, where Ra is defined above) was in a suitable solvent such as ethyl ether or DME or tetrahydrofuran or DMF using suitable base such as sodium hydroxide or potassium hydroxide or lithium hydroxide at temperatures ranging from –78° C. to 25° C. to provide the 6-iodo-7-alkyl-7H-pyrrolo[3,2-f]quinazoline-1,3-diamine VII.

Compound VIII: The resultant 6-iodo-7-alkyl-7H-pyrrolo[3,2-f]quinazoline-1,3-diamine VII are then further alkylated at –50° C. to room temperature in a suitable solvent such as ethyl ether or DME or tetrahydrofuran or DMF using with suitable base such as sodium hydride and a variety of halides (e.g., $R_1$Br, $R_2$Br, $R_3$Br or $R_1$I, $R_2$I, $R_3$I, where $R_1$, $R_2$, $R_3$ are defined above) yielding mono-, di- or tri substituted the 6-iodo-7-alkyl-7H-pyrrolo[3,2-f]quinazoline-1,3-diamine VIII.

Compound IX: The coupling reaction can be carried out by a conventional aryl coupling method, e.g., Suzuki coupling method: (a) Suzuki et al., *Synth. Commun.* 1981, 11, 513, (b) Suzuki, *Pure and Appl. Chem.* 1985, 57, 1749–1758, (c) Suzuki et al., *Chem. Rev.* 1995, 95, 2457–2483, (d) Shieh et al., *J. Org. Chem.* 1992, 57, 379–381, (e) Martin et al., *Acta Chemica Scandinavica.* 1993, 47, 513.

Typical conditions used to carry out the Suzuki coupling of VIII include the use of either aryl or heteroaromatic boronic acid or esters (e.g., where Ar is defined as aryl) as coupling partner, in aqueous base such as sodium bicarbonate or potassium carbonate or barium hydroxide or triethylamine solution, a palladium catalyst (2–20 mole %) such as tetrakis(triphenylphosphine)-palladium (0) or [1,1'-bis(diphenylphosphino)-ferrocene]dichloro-palladium(II), in a suitable solvent such as aqueous ethanol or THF or DMF or ethyleneglycol for at temperatures ranging from 25° C. to 125° C. for 2–18 hr yields compound the 6-aryl substituted 7-alkyl-7H-pyrrolo[3,2-f]quinazoline-1,3-diamine IX.

Alternatively, coupling reaction can be carried out by a conventional aryl or heteroaromatic coupling partner utilizing Stille coupling. e.g., Stille et al., *Angew. Chem. Int. Ed. Engl.*, 1986, 25, 508.

Typical conditions used to carry out the Stille reaction include the use of an organostannane as the coupling partner, palladium catalyst (2–20 mole %) such as tetrakis(triphenylphosphine)-palladium (0) or [1,1'bis(diphenylphosphino)-ferrocene]dichloro-palladium(II), a salt such as potassium fluoride or lithium chloride, in a suitable anhydrous solvent such as THF or DMF or ethylene glycol for at temperatures ranging from 25° C. to 125° C. for 2–18 hr yields 6-aryl substituted 7-alkyl-7H-pyrrolo[3,2-f]quinazoline-1,3-diamine IX.

Scheme 3 below provides an alternatively general synthesis steps, and the examples provide a detailed description of the schematic methods suitable solvent such as aqueous ethanol or THF or DMF or ethylene glycol for at temperatures ranging from 25° C. to 125° C. for 2–18 hr yields compound X. Alternatively, coupling reaction can be carried out by a conventional aryl or heteroaromatic coupling partner utilizing Stille coupling. e.g. Stille et al., *Angew. Chem. Int. Ed. Engl.*, 1986, 25, 508.

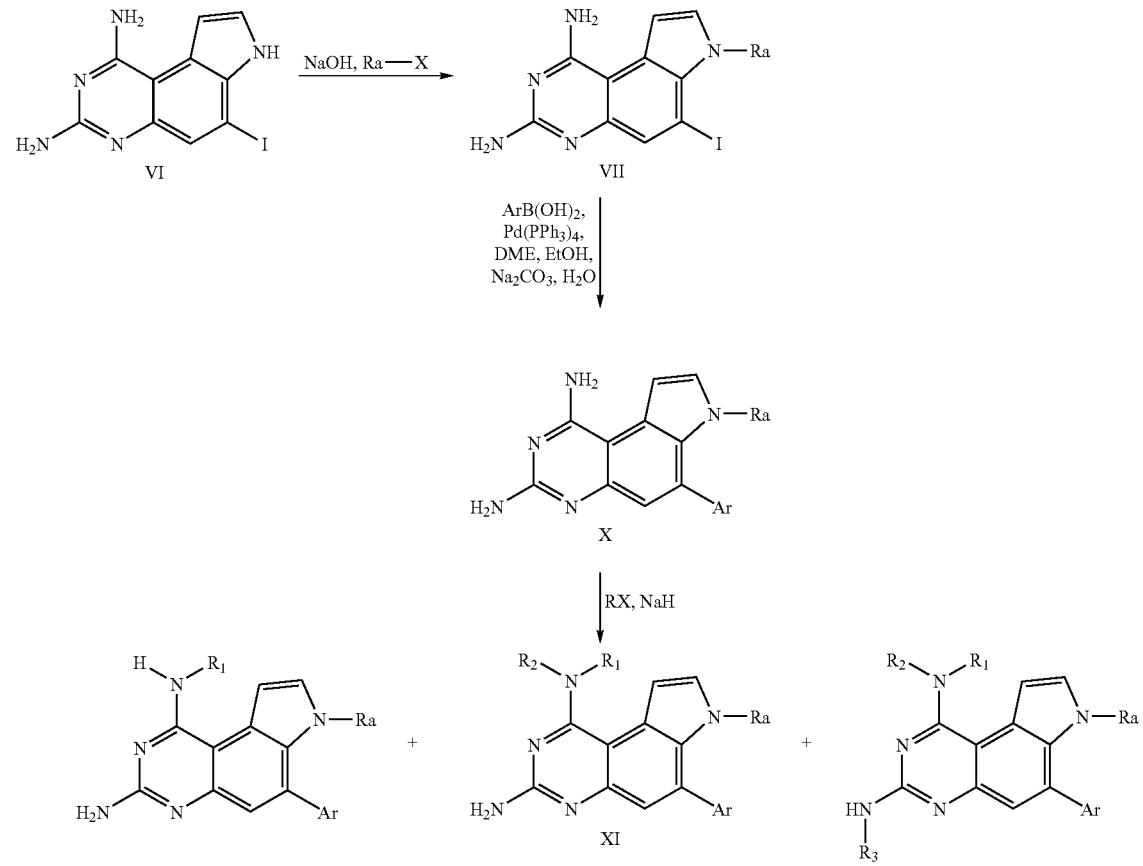

SCHEME 3

Compound VII: Typical condition used to carry out alkylation of derivatives VI with variety of halides (e.g. RaBr or RaI, where Ra is defined above) is carried out with suitable solvent such as tetrahydrofuran, DMF using suitable base such as sodium hydroxide at temperatures ranging from −78° C. to 25° C. to provide the 6-iodo-7-alkyl-7H-pyrrolo[3,2-f]quinazoline-1,3-diamine VII.

Compound X: The coupling reaction can be carried out by a conventional aryl coupling method, e.g., Suzuki coupling method: (a) Suzuki et al., *synth. commun.* 1981, 11, 513, (b) Suzuki *pure and Appl. Chem.* 1985, 57, 1749–1758, (c) Suzuki et al., *Chem. Rev.* 1995, 95, 2457–2483, (d) Shieh et al., *J. Org. Chem.* 1992, 57, 379–381, (e) Martin et al., *Acta Chemica Scandinavica.* 1993, 47, 513.

Typical conditions used to carry out the Suzuki coupling of VII includes the use of either aryl or heteroaromatic boronic acid or esters (e.g. where Ar is defined as aryl) as coupling partner, in aqueous base such as sodium bicarbonate or potassium carbonate or barium hydroxide or triethylamine solution, a palladium catalyst (2–20 mole %) such as tetrakis(triphenylphosphine)-palladium (0) or [1,1'bis(diphenylphosphino)-ferrocene]dichloro-palladium(II), in a Typical conditions used to carry out the Stille reaction include the use of an organostannane as the coupling partner, palladium catalyst (2–20 mole %) such as tetrakis(triphenylphosphine)-palladium (0) or [1,1'bis(diphenylphosphino)-ferrocene]dichloro-palladium(II), a salt such as potassium fluoride or lithium chloride, in a suitable anhydrous solvent such as THF or DMF or ethylene glycol for at temperatures ranging from 25° C. to 125° C. for 2–18 hr yields compound X.

Compound XI: The compound X is then further alkylated at to −50° C. to room temperature with suitable base such as sodium hydride and variety of halides (e.g., $R_1Br$, $R_2Br$, $R_3Br$ or $R_1I$, $R_2I$, $R_3I$, where $R_1$, $R_2$, $R_3$ are defined above) yields mono-, di- or tri substituted compounds XI. The control of alkylation can be controlled by selecting the appropriate equivalence of the halide used.

The invention is illustrated by the following Examples. In the Examples, Examples 2–22 was carried out by the procedure of Example 1 and Examples 24–42 was carried out by the procedure of Example 23.

EXAMPLES

Example 1

(A) 2-(3-amino-7-methyl-6-thiophen-2-yl-7H-pyrrolo[3,2-f]quinazolin-1-ylamino)-ethanol trifluoroacetic acid salt

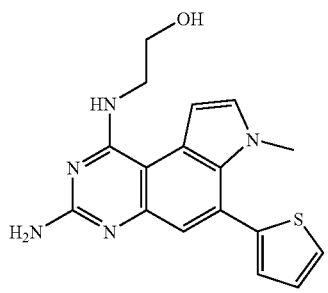

A solution 6-iodo-7H-pyrrolo[3,2-f]quinazoline-1,3-diamine VI (2.68 g, 8.24 mmol) in tetrahydrofuran (100 mL) was treated with powdered sodium hydroxide (0.66 g, 16.5 mmol), iodomethane (0.62 mL, 9.96 mmol), and tetrabutylammonium bromide (0.8 g, 2.48 mmol) and the resulting mixture stirred at 25° C. for 18 h. The resulting mixture was concentrated in vacuo. The residue was partitioned between methylene chloride (70 mL) and water (70 mL) and this mixture was stirred at 25° C. for 30 min. The precipitate was isolated by filtration, washed with water, and dried in vacuo to afford 6-iodo-7-methyl-7H-pyrrolo[3,2-f]quinazoline-1,3-diamine (2.67 g, 95.5%) as a yellow solid; $^1$H NMR (DMSO-$d_6$, 300 MHz) δ 7.58 (s, 1H), 7.47 (d, J=2.93 Hz, 1H), 6.99 (d, J=2.93 Hz, 1H), 6.78 (broad s, 2H), 5.83 (broad s, 2H), 4.16 (s, 3H).

A solution of 6-iodo-7-methyl-7H-pyrrolo[3,2-f]quinazoline-1,3-diamine (580 mg, 1.71 mmol) in tetrahydrofuran (20 mL) and N,N-dimethylformamide (10 mL) was cooled to −50° C. and treated with 60% sodium hydride (270 mg, 6.84 mmol). The reaction mixture was warmed to −20° C. and allowed to stir for 20 min. before being re-cooled to −50° C. 2-(2-bromoethoxy)tetrahydro-2-H-pyran (300 mg, 1.88 mmol) was added, the cooling bath removed, and the resulting mixture was allowed to stir at 25° C. for 6 h. The reaction mixture was then recooled to −4° C. and treated with another portion of 60% sodium hydride (270 mg, 6.84 mmol) followed by another portion of 2-(2-bromoethoxy)tetrahydro-2-H-pyran (300 mg, 1.88 mmol). The resulting mixture was allowed to stir at 25° C. for 2 d, and then concentrated in vacuo. HPLC purification (4 runs on a 21.2 mm×100 mm Zorbax CombiHT column using a 5:95 to 95:5 acetonitrile:water: 0.75% TFA gradient over 15 minutes) afforded 2-(3-amino-6-iodo-7-methyl-7H-pyrrolo[3,2-f]quinazolin-1-ylamino)-ethanol trifluoroactic acid salt (270 mg, 32%) as an off-white solid; LRMS for freebase $C_{13}H_{14}IN_5O$ (M+H)$^+$ at m/z=384.

A solution of 2-(3-amino-6-iodo-7-methyl-7H-pyrrolo[3,2-f]quinazolin-1-ylamino)-ethanol trifluoroactic acid salt (90 mg, 0.23 mmol) in ethylene glycol dimethyl ether (8.0 mL) and ethanol (4.0 mL) at 25° C. was treated with thiophene-2-boronic acid (60 mg, 0.47 mmol), a 2.0 M aqueous sodium bicarbonate solution (2.0 mL), and tetrakis(triphenylphosphine)-palladium (0) (5.0 mg). The resulting mixture was heated to reflux for 18 h. The resulting mixture was concentrated in vacuo and the residue suspended in acetonitrile and water and filtered. HPLC purification (21.2 mm×100 mm Zorbax CombiHT column using a 5:95 to 95:5 acetonitrile:water: 0.75% TFA gradient over 15 minutes) afforded 2-(3-amino-7-methyl-6-thiophen-2-yl-7H-pyrrolo [3,2-f]quinazolin-1-ylamino)-ethanol trifluoro-acetic acid salt as a light yellow solid; LRMS for $C_{17}H_{17}N_5O$ (M+H)$^+$ at m/z=340.

Example 2

In an analogous manner, there were obtained

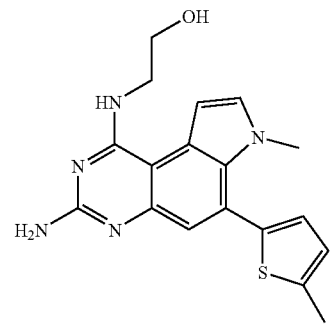

from 2-(3-amino-6-iodo-7-methyl-7H-pyrrolo[3,2-f]quinazolin-1-ylamino)-ethanol trifluoroactic acid salt and 5-methylthiophene-2-boronic acid there was produced 2-[3-Amino-7-methyl-6-(5-methyl-thiophen-2-yl)-7H-pyrrolo[3,2-f]quinazolin-1-ylamino]-ethanol trifluoro-acetic acid salt as an off-white solid; LRMS for $C_{18}H_{19}N_5OS$ (M+H)$^+$ at m/z=354.

Example 3

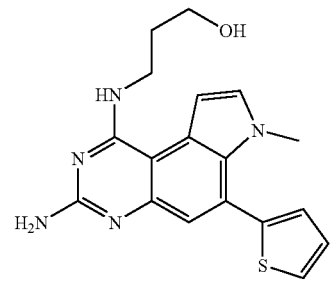

From 3-(3-Amino-6-iodo-7-methyl-7H-pyrrolo[3,2-f]quinazolin-1-ylamino)-propan-1-ol trifluoro-acetic acid salt and thiophene-2-boronic acid there was produced 3-(3-Amino-7-methyl-6-thiophen-2-yl-7H-pyrrolo[3,2-f]quinazolin-1-ylamino)-propan-1-ol trifluoro-acetic acid salt as an off-white solid; LRMS for $C_{18}H_{19}N_5OS$ (M+H)$^+$ at m/z=354.

Example 4

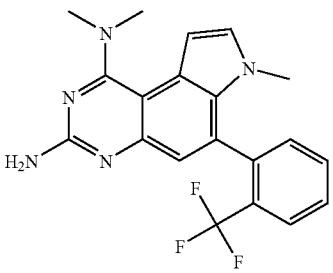

From 6-Iodo-7,N1,N1-trimethyl-7H-pyrrolo[3,2-f]quinazoline-1,3-diamine and 2-(trifluoromethyl)benzeneboronic acid there was produced 7,N1,N1-Trimethyl-6-(2-trifluoromethyl-phenyl)-7H-pyrrolo[3,2-f]quinazoline-1,3-diamine trifluoro-acetic acid salt as a white solid; LRMS for $C_{20}H_{18}F_3N_5$ $(M+H)^+$ at m/z=386.

Example 5

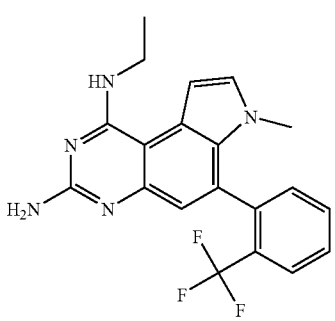

From N1-Ethyl-6-iodo-7-methyl-7H-pyrrolo[3,2-f]quinazoline-1,3-diamine trifluoro-acetic acid salt and 2-(trifluoromethyl)benzeneboronic acid there was produced N1-Ethyl-7-methyl-6-(2-trifluoromethyl-phenyl)-7H-pyrrolo[3,2-f]quinazoline-1,3-diamine trifluoro-acetic acid salt as a white solid; LRMS for $C_{20}H_{18}F_3N_5$ $(M+H)^+$ at m/z=386.

Example 6

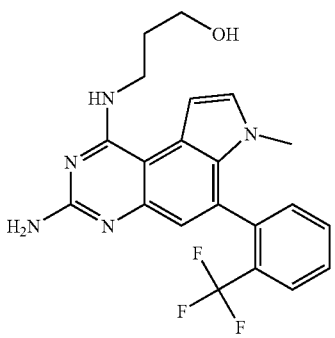

Example 6 From 3-(3-Amino-6-iodo-7-methyl-7H-pyrrolo[3,2-f]quinazolin-1-ylamino)-propan-1-ol trifluoro-acetic acid salt and 2-(trifluoromethyl)benzeneboronic acid there was produced 3-[3-Amino-7-methyl-6-(2-trifluoromethyl-phenyl)-7H-pyrrolo[3,2-f]quinazolin-1-ylamino]-propan-1-ol trifluoro-acetic acid salt as an off-white solid; LRMS for $C_{21}H_{20}F_3N_5O$ $(M+H)^+$ at m/z=416.

Example 7

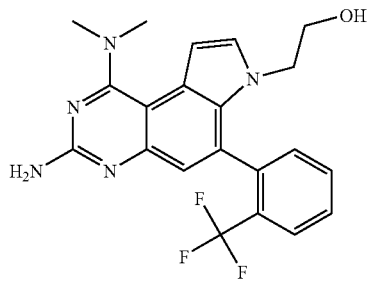

From 2-(3-Amino-1-dimethylamino-6-iodo-pyrrolo[3,2-f]quinazolin-7-yl)-ethanol trifluoro-acetic acid salt and 2-(trifluoromethyl)benzeneboronic acid there was produced 2-[3-Amino-1-dimethylamino-6-(2-trifluoromethyl-phenyl)-pyrrolo[3,2-f]quinazolin-7-yl]-ethanol trifluoro-acetic acid salt as an off-white solid; LRMS for $C_{21}H_{20}F_3N_5O$ $(M+H)^+$ at m/z=416.

Example 8

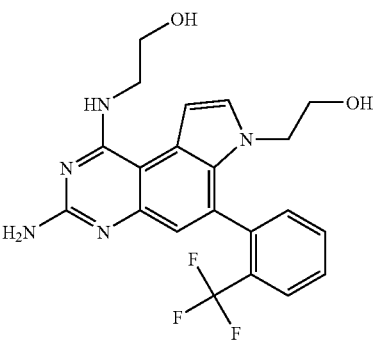

From 2-[3-Amino-7-(2-hydroxy-ethyl)-6-iodo-7H-pyrrolo[3,2-f]quinazolin-1-ylamino]-ethanol trifluoro-acetic acid salt and 2-(trifluoromethyl)benzeneboronic acid there was produced 2-[3-Amino-7-(2-hydroxy-ethyl)-6-(2-trifluoromethyl-phenyl)-7H-pyrrolo[3,2-f]quinazolin-1-ylamino]-ethanol trifluoro-acetic acid salt as an off-white solid; LRMS for $C_{21}H_{20}F_3N_5O_2$ $(M+H)^+$ at m/z=432.

Example 9

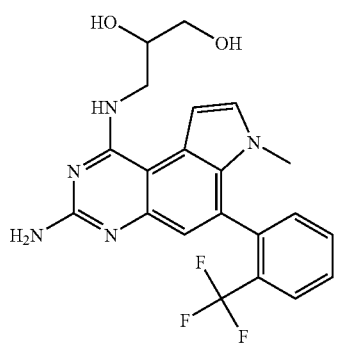

From 3-(3-Amino-6-iodo-7-methyl-7H-pyrrolo[3,2-f]quinazolin-1-ylamino)-propane-1,2-diol trifluoro-acetic acid salt and 2-(trifluoromethyl)benzeneboronic acid there was produced 3-[3-Amino-7-methyl-6-(2-trifluoromethyl-phenyl)-7H-pyrrolo[3,2-f]quinazolin-1-ylamino]-propane-1,2-diol trifluoro-acetic acid salt as an off-white solid; LRMS for $C_{21}H_{20}F_3N_5O_2$ (M+H)$^+$ at m/z=432.

Example 10

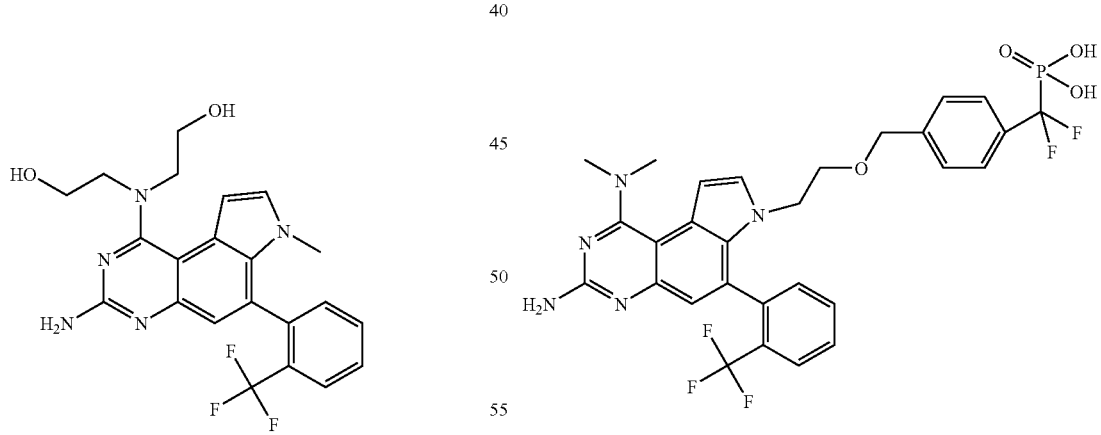

From 2-[(3-Amino-6-iodo-7-methyl-7H-pyrrolo[3,2-f]quinazolin-1-yl)-(2-hydroxy-ethyl)-amino]-ethanol trifluoro-acetic acid salt and 2-(trifluoromethyl)benzeneboronic acid there was produced 2-[[3-Amino-7-methyl-6-(2-trifluoromethyl-phenyl)-7H-pyrrolo[3,2-f]quinazolin-1-yl]-(2-hydroxy-ethyl)-amino]-ethanol trifluoro-acetic acid salt as a light yellow solid; LRMS for $C_{22}H_{22}F_3N_5O_2$ (M+H)$^+$ at m/z=446.

Example 11

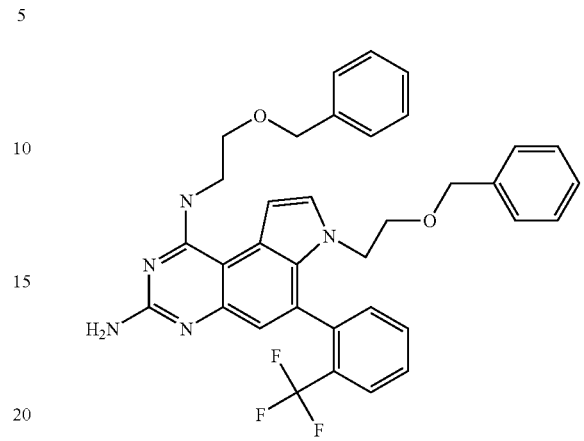

From 7,N1-Bis-(2-benzyloxy-ethyl)-6-iodo-7H-pyrrolo[3,2-f]quinazoline-1,3-diamine trifluoro-acetic acid salt and 2-(trifluoromethyl)benzeneboronic acid there was produced 7,N1-Bis-(2-benzyloxy-ethyl)-6-(2-trifluoromethyl-phenyl)-7H-pyrrolo[3,2-f]quinazoline-1,3-diamine trifluoro-acetic acid salt as a light yellow solid; LRMS for $C_{35}H_{32}F_3N_5O_2$ (M+H)$^+$ at m/z=612.

Example 12

From ({4-[2-(3-Amino-1-dimethylamino-6-iodo-pyrrolo[3,2-f]quinazolin-7-yl)-ethoxymethyl]-phenyl}-difluoro-methyl)-phosphonic acid and 2-(trifluoromethyl)benzeneboronic acid there was produced [(4-{2-[3-Amino-1-dimethylamino-6-(2-trifluoromethyl-phenyl)-pyrrolo[3,2-f]quinazolin-7-yl]-ethoxymethyl}-phenyl)-difluoro-methyl]-phosphonic acid as a light yellow solid; LRMS for $C_{29}H_{27}F_5N_5O_4P$ (M+H)$^+$ at m/z=636.

Example 13

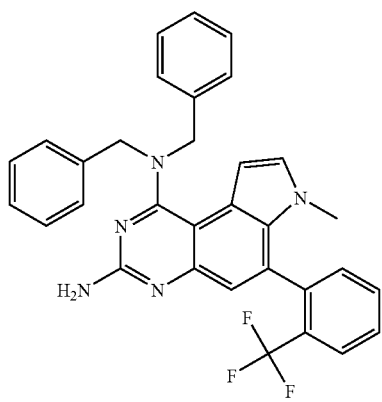

From N1,N1-Dibenzyl-6-iodo-7-methyl-7H-pyrrolo[3,2-f]quinazoline-1,3-diamine trifluoro-acetic acid salt and 2-(trifluoromethyl)benzeneboronic acid there was produced N1,N1-Dibenzyl-7-methyl-6-(2-trifluoromethyl-phenyl)-7H-pyrrolo[3,2-f]quinazoline-1,3-diamine trifluoro-acetic acid salt as a white solid; LRMS for $C_{32}H_{26}F_3N_5$ (M+H)$^+$ at m/z=538.

Example 14

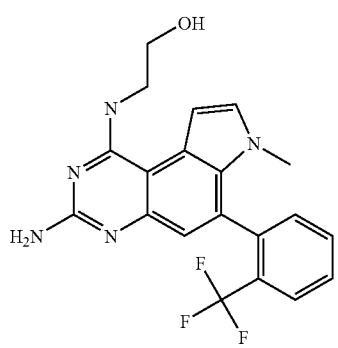

From 2-(3-Amino-6-iodo-7-methyl-7H-pyrrolo[3,2-f]quinazolin-1-ylamino)-ethanol trifluoro-acetic acid salt and 2-(trifluoromethyl)benzeneboronic acid there was produced 2-[3-Amino-7-methyl-6-(2-trifluoromethyl-phenyl)-7H-pyrrolo[3,2-f]quinazolin-1-ylamino]-ethanol trifluoro-acetic acid salt as an off-white solid; LRMS for $C_{20}H_{18}F_3N_5O$ (M+H)$^+$ at m/z=402.

Example 15

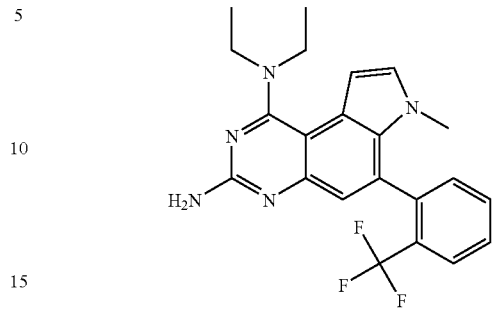

From N1,N1-Diethyl-6-iodo-7-methyl-7H-pyrrolo[3,2-f]quinazoline-1,3-diamine trifluoro-acetic acid salt and 2-(trifluoromethyl)benzeneboronic acid there was produced N1,N1-Diethyl-7-methyl-6-(2-trifluoromethyl-phenyl)-7H-pyrrolo[3,2-f]quinazoline-1,3-diamine trifluoro-acetic acid salt as an off-white solid; (ES)$^+$-HRMS m/e calcd for $C_{22}H_{19}N_5F_6$ (M+H)$^+$ 468.1617, found 468.1618.

Example 16

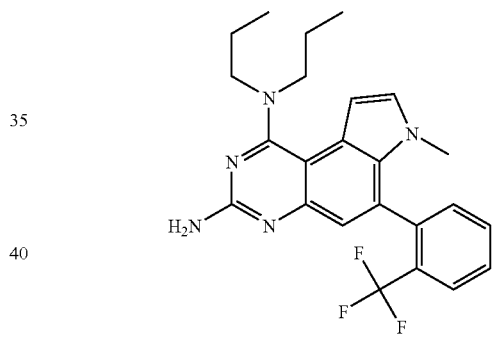

From 6-Iodo-7-methyl-N1,N1-dipropyl-7H-pyrrolo[3,2-f]quinazoline-1,3-diamine trifluoro-acetic acid salt and 2-(trifluoromethyl)benzeneboronic acid there was produced 7-Methyl-N1,N1-dipropyl-6-(2-trifluoromethyl-phenyl)-7H-pyrrolo[3,2-f]quinazoline-1,3-diamine trifluoro-acetic acid salt as a white solid; LRMS for $C_{24}H_{26}F_3N_5$ (M+H)$^+$ at m/z=442.

Example 17

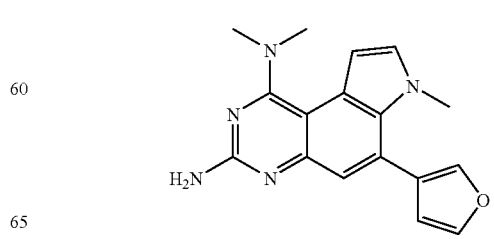

From 6-Iodo-7,N1,N1-trimethyl-7H-pyrrolo[3,2-f]quinazoline-1,3-diamine and furan-3-boronic acid there was produced 6-Furan-3-yl-7,N1,N1-trimethyl-7H-pyrrolo[3,2-f]quinazoline-1,3-diamine; EI-HRMS m/e calcd for $C_{17}H_{17}N_5O$ (M$^+$) 307.1433, found 307.1427.

Example 18

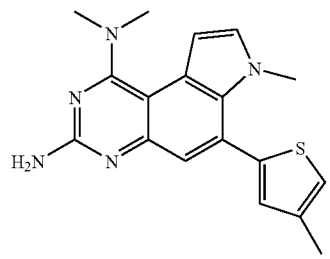

From 6-Iodo-7,N1,N1-trimethyl-7H-pyrrolo[3,2-f]quinazoline-1,3-diamine and 4-methylthiophene-2-boronic acid there was produced 7,N1,N1-Trimethyl-6-(4-methyl-thiophen-2-yl)-7H-pyrrolo[3,2-f]quinazoline-1,3-diamine; (ES)$^+$-HRMS m/e calcd for $C_{18}H_{19}N_5S$ (M$^+$) 337.1361, found 337.1357.

Example 19

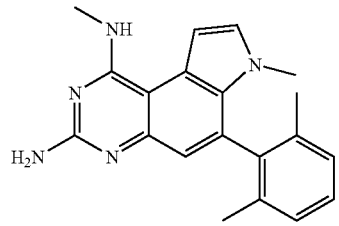

From 6-Iodo-7,N1,N1-trimethyl-7H-pyrrolo[3,2-f]quinazoline-1,3-diamine and 1-(t-butoxycarbonyl)pyrrole-2-boronic acid there was produced 2-(3-Amino-1-dimethylamino-7-methyl-7H-pyrrolo[3,2-f]quinazolin-6-yl)-pyrrole-1-carboxylic acid tert-butyl ester; EI-HRMS m/e calcd for $C_{22}H_{26}N_6O_2$ (M$^+$) 406.2117, found 406.2115.

Example 20

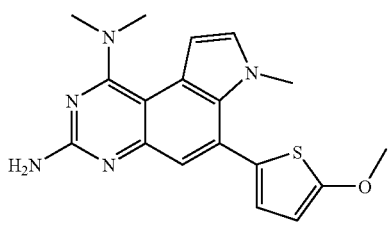

From 6-Iodo-7,N1,N1-trimethyl-7H-pyrrolo[3,2-f]quinazoline-1,3-diamine and 5-methoxy-2-thiopheneboronic acid there was produced 6-(5-Methoxy-thiophen-2-yl)-7,N1,N1-trimethyl-7H-pyrrolo[3,2-f]quinazoline-1,3-diamine; EI-HRMS m/e calcd for $C_{18}H_{19}N_5OS$ (M$^+$) 353.1310, found 353.1306.

Example 21

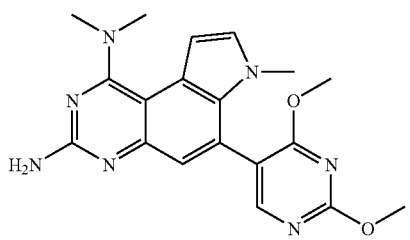

From 6-Iodo-7,N1-dimethyl-7H-pyrrolo[3,2-f]quinazoline-1,3-diamine and 2,6-dimethylphenylboronic acid there was produced 6-(2,6-Dimethyl-phenyl)-7,N1-dimethyl-7H-pyrrolo[3,2-f]quinazoline-1,3-diamine trifluoro-acetic acid salt as an off-white solid; EI-HRMS m/e calcd for $C_{20}H_{21}N_5$ (M$^+$) 331.1797, found 331.1786.

Example 22

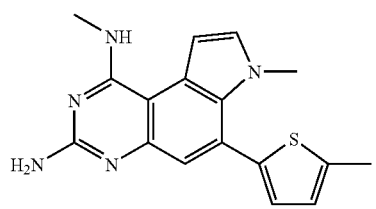

From 6-Iodo-7,N1,N1-trimethyl-7H-pyrrolo[3,2-f]quinazoline-1,3-diamine and 2,4-dimethoxypyrimidine-5-boronic acid there was produced 6-(2,4-Dimethoxy-pyrimidin-5-yl)-7,N1,N1-trimethyl-7H-pyrrolo[3,2-f]quinazoline-1,3-diamine as a white solid; EI-HRMS m/e calcd for $C_{19}H_{21}N_7O_2$ (M$^+$) 379.1757, found 379.1763.

Example 23

7, N1-Dimethyl-6-(5-methyl-thiophen-2-yl)-7H-pyrrolo[3,2-f]quinazoline-1,3-diamine A solution of 6-iodo-7H-pyrrolo[3,2-f]quinazoline-1,3-diamine (prepared as in Example 1, 400 mg, 1.23 mmol) in tetrahydrofuran (20 mL) at 25° C. was treated with sodium hydroxide (98 mg, 2.46 mmol), methyl iodide (0.09 mL, 1.48 mmol), and tetrabutylammonium bromide (198 mg, 0.62 mmol and stirred at 25° C. for 18 h. The resulting mixture was treated with ethyl acetate, water, and a saturated aqueous sodium chloride solution, shaken and separated. The aqueous layer was extracted with ethyl acetate and the combined organic layers were dried over sodium sulfate, filtered, and concentrated in vacuo to afford 6-iodo-7-methyl-7H-pyrrolo[3,2-f]quinazoline-1,3-diamine (500 mg) as a yellow solid. The product was taken on into the next reaction without further purification.

A mixture of 6-iodo-7-methyl-7H-pyrrolo[3,2-f]quinazoline-1,3-diamine (600 mg, 1.77 mmol), 2-(thiophene)benzeneboronic acid (321 mg, 2.20 mmol), tetrakis(triphenylphosphine)-palladium (0) (231 mg, 0.2 mmol) in ethanol (6.0 mL), ethylene glycol dimethyl ether (6.0 mL), and a saturated aqueous sodium carbonate solution (3.0 mL) was heated at reflux for 18 h. The resulting mixture was poured into water and extracted with a solution of 9/1 methylene chloride/methanol. The organic layers were combined and dried over magnesium sulfate, filtered, and dried in vacuo. Biotage chromatography (FLASH 12M, Silica, 9:1 methylene chloride/methanol) afforded 7-methyl-6-(5-methyl-thiophen-2-yl)-7H-pyrrolo[3,2-f]quinazoline-1,3-diamine (190 mg, 34.8%) as a solid; EI-HRMS m/e calcd for $C_{16}H_{15}N_5S$ $(M+H)^+$ 310.1121, found 310.1125.

A solution of 7-methyl-6-(5-methyl-thiophen-2-yl)-7H-pyrrolo[3,2-f]quinazoline-1,3-diamine (100 mg, 0.32 mmol) in N,N-dimethylformamide (5.0 mL) at 25° C. was treated with 60% sodium hydride (25 mg, 0.62 mmol) and iodomethane (0.62 mL, 0.35 mmol) and stirred at 25° C. for 15 min. The resulting mixture was poured into water and extracted with a 9/1 methylene chloride/methanol solution. Flash chromatography (Merck Silica gel 60, 230–400 mesh, 9:1 methylene chloride/methanol) afforded 7,N1-dimethyl-6-(5-methyl-thiophen-2-yl)-7H-pyrrolo[3,2-f]quinazoline-1,3-diamine (12 mg, 11.5%) as a light yellow solid; EI-HRMS m/e calcd for $C_{17}H_{17}N_5S$ $(M+H)^+$ 324.1278, found 324.1280; and 7,N1,N1-trimethyl-6-(5-methyl-thiophen-2-yl)-7H-pyrrolo[3,2-f]quinazoline-1,3-diamine (18 mg, 16.5%) as a dark brown solid; EI-HRMS m/e calcd for $C_{18}H_{19}N_5S$ $(M+H)^+$ 338.1434, found 338.1437.

Example 24

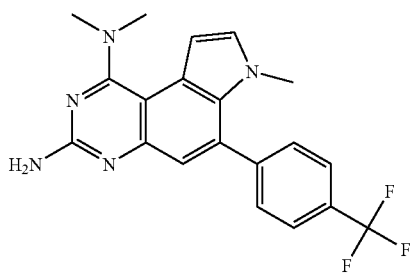

From 6-(4-Trifluoromethyl-phenyl)-7H-pyrrolo[3,2-f]quinazoline-1,3-diamine there was produced 7,N1,N1-Trimethyl-6-(4-trifluoromethyl-phenyl)-7H-pyrrolo[3,2-f]quinazoline-1,3-diamine; EI-HRMS m/e calcd for $C_{20}H_{18}F_3N_5$ $(M^+)$ 385.1517, found 385.1514.

Example 25

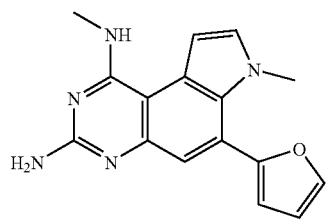

From 6-Furan-2-yl-7H-pyrrolo[3,2-f]quinazoline-1,3-diamine there was produced 6-Furan-2-yl-7,N1-dimethyl-7H-pyrrolo[3,2-f]quinazoline-1,3-diamine trifluoro-acetic acid salt as a light yellow solid; EI-HRMS m/e calcd for $C_{16}H_{15}N_5O$ $(M^+)$ 293.1277, found 293.1280.

Example 26

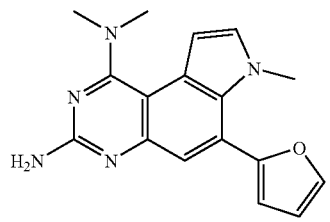

From 6-Furan-2-yl-7H-pyrrolo[3,2-f]quinazoline-1,3-diamine:6-Furan-2-yl-7,N1,N1-trimethyl-7Hpyrrolo[3,2-f]quinazoline-1,3-diamine as a yellow solid; EI-HRMS m/e calcd for $C_{17}H_{17}N_5O$ $(M^+)$ 307.1433, found 307.1434

Example 27

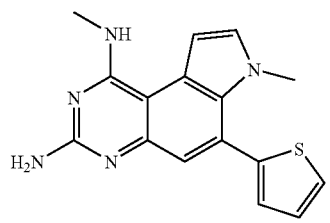

From 6-Thiophen-2-yl-7H-pyrrolo[3,2-f]quinazoline-1,3-diamine trifluoro-acetic acid salt there was produced 7,N1-Dimethyl-6-thiophen-2-yl-7H-pyrrolo[3,2-f]quinazoline-1,3-diamine trifluoro-acetic acid salt as a light yellow solid; LRMS for $C_{16}H_{15}N_5S$ $(M+H)^+$ at m/z=310.

Example 28

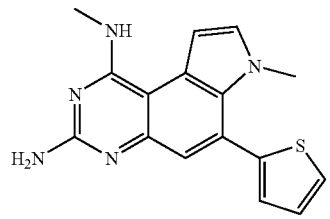

From 6-thiophene-2-yl-7H-pyrrolo[3,2-f]quinazoline-1,3-diamine there was produced 7-Ethyl-N1-methyl-6-thiophen-2-yl-7H-pyrrolo[3,2-f]quinazoline-1,3-diamine trifluoro-acetic acid salt; (ES)$^+$-HRMS m/e calcd for $C_{17}H_{17}N_5S$ (M+H)$^+$ 324.1277, found 324.1281.

Example 29

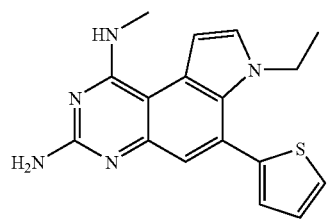

From 7-Methyl-6-(5-methyl-thiophen-2-yl)-7H-pyrrolo[3,2-f]quinazoline-1,3-diamine: 7,N1,N1-Trimethyl-6-thiophen-2-yl)-7H-pyrrolo[3,2-f]quinazoline-1,3-diamine as a yellow solid; EI-HRMS m/e calcd for $C_{17}H_{17}N_5S$ (M$^+$) 323.1205, found 323.1209

Example 30

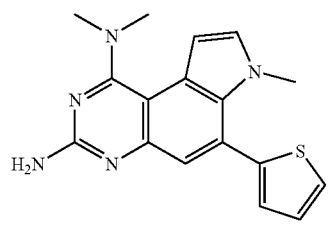

From 7-Methyl-6-(5-methyl-thiophen-2-yl)-7H-pyrrolo[3,2-f]quinazoline-1,3-diamine: 7,N1,N1-Trimethyl-6-thiophen-2-yl)-7H-pyrrolo[3,2-f]quinazoline-1,3-diamine as a yellow solid; EI-HRMS m/e calcd for $C_{17}H_{17}N_5S$ (M$^+$) 323.1205, found 323.

Example 31

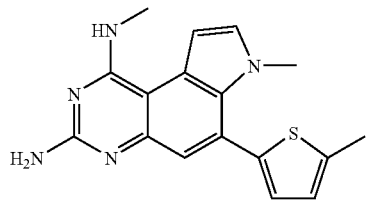

From 7-Methyl-6-thiophen-2-yl-7H-pyrrolo[3,2-f]quinazoline-1,3-diamine there was produced 7,N1-Dimethyl-6-(5-methyl-thiophen-2-yl)-7H-pyrrolo[3,2-f]quinazoline-1,3-diamine as a yellow solid; (ES)$^+$-HRMS m/e calcd for $C_{17}H_{17}N_5S$ (M+H)$^+$ 324.1278, found 324.1280.

Example 32

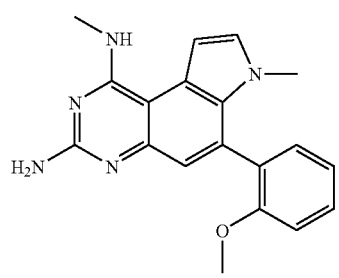

From 7-Methyl-6-(2-Methoxy-phenyl)-7H-pyrrolo[3,2-f]quinazoline-1,3-diamine there was produced 6-(2-Methoxy-phenyl)-7,N1-dimethyl-7H-pyrrolo[3,2-f]quinazoline-1,3-diamine trifluoro-acetic acid salt as a white solid; LCMS for $C_{19}H_{19}N_5O$ (M+)$^+$ at m/z=333

Example 33

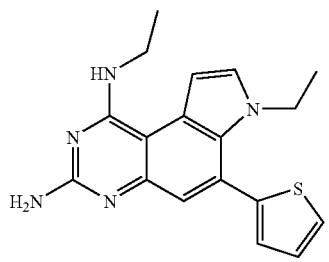

From 7-Ethyl-6-thiophen-2-yl-7H-pyrrolo[3,2-f]quinazoline-1,3-diamine there was produced 7,N1-Diethyl-6-thiophen-2-yl-7H-pyrrolo[3,2-f]quinazoline-1,3-diamine trifluoro-acetic acid salt; (ES)$^+$-HRMS m/e calcd for $C_{18}H_{19}N_5S$ (M+H)$^+$ 338.1434, found 338.1437.

Example 34

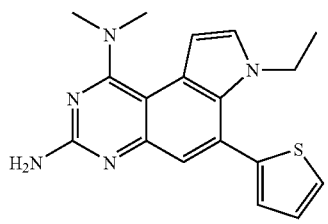

From 7-Ethyl-6-thiophen-2-yl-7H-pyrrolo[3,2-f]quinazoline-1,3-diamine there was produced 7-Ethyl-N1,N1-dimethyl-6-thiophen-2-yl-7H-pyrrolo[3,2-f]quinazoline-1,3-diamine trifluoro-acetic acid salt; (ES)$^+$-HRMS m/e calcd for C$_{18}$H$_{19}$N$_5$S (M+H)$^+$ 338.1434, found 338.1437.

Example 35

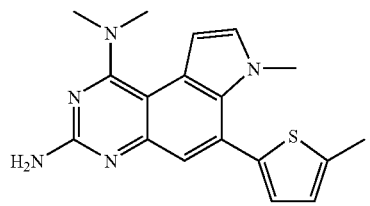

From 7-Methyl-6-(5-methyl-thiophen-2-yl)-7H-pyrrolo[3,2-f]quinazoline-1,3-diamine there was produced 7,N1,N1-Trimethyl-6-(5-methyl-thiophen-2-yl)-7H-pyrrolo[3,2-f]quinazoline-1,3-diamine as a yellow solid; (ES)$^+$-HRMS m/e calcd for C$_{18}$H$_{19}$N$_5$S (M+H)$^+$ 338.1434, found 338.1437.

Example 36

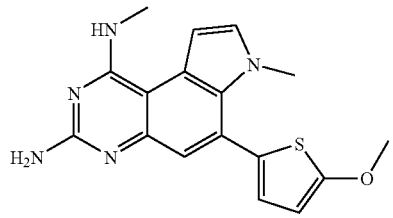

From 6-(5-Methoxy-thiophen-2-yl)-7-methyl-7H-pyrrolo[3,2-f]quinazoline-1,3-diamine there was produced 6-(5-Methoxy-thiophen-2-yl)-7,N1,N1-dimethyl-7H-pyrrolo[3,2-f]quinazoline-1,3-diamine as a white solid; EI-HRMS m/e calcd for C$_{17}$H$_{17}$N$_5$OS (M$^+$) 339.1154, found 339.1159.

Example 37

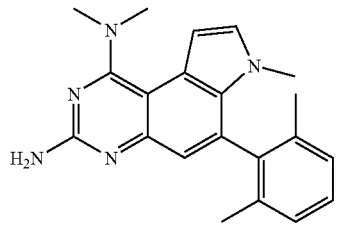

From 6-(2,6-Dimethyl-phenyl)-7-methyl-7H-pyrrolo[3,2-f]quinazoline-1,3-diamine there was produced 6-(2,6-Dimethyl-phenyl)-7,N1,N1-trimethyl-7H-pyrrolo[3,2-f]quinazoline-1,3-diamine trifluoro-acetic acid salt as an off-white solid; EI-HRMS m/e calcd for C$_{21}$H$_{23}$N$_5$ (M$^+$) 345.1953, found 345.1958.

Example 38

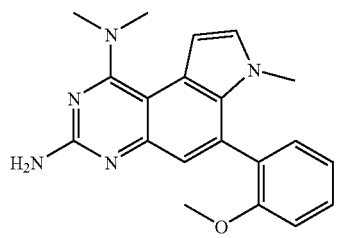

From 6-(2-Methoxy-phenyl)-7-methyl-7H-pyrrolo[3,2-f]quinazoline-1,3-diamine there was produced 6-(2-Methoxy-phenyl)-7,N1,N1-trimethyl-7H-pyrrolo[3,2-f]quinazoline-1,3-diamine trifluoro-acetic acid salt as a white solid; EI-HRMS m/e calcd for C$_{20}$H$_{21}$N$_5$O (M$^+$) 347.1746, found 347.1739.

Example 39

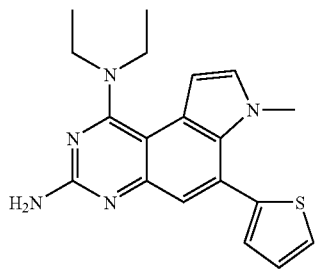

From 7-Methyl-6-thiophen-2-yl-7H-pyrrolo[3,2-f]quinazoline-1,3-diamine there was produced N1,N1-Diethyl-7-methyl-6-thiophen-2-yl-7H-pyrrolo[3,2-f]quinazoline-1,3-diamine trifluoro-acetic acid salt as a light yellow solid; EI-HRMS m/e calcd for C$_{19}$H$_{21}$N$_5$S (M$^+$) 351.1518, found 351.1517.

Example 40

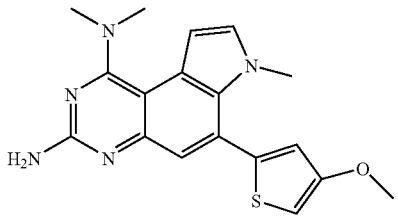

From 6-(4-Methoxy-thiophen-2-yl)-7-methyl-7H-pyrrolo[3,2-f]quinazoline-1,3-diamine there was produced 6-(4-Methoxy-thiophen-2-yl)-7,N1,N1-trimethyl-7H-pyrrolo[3,2-f]quinazoline-1,3-diamine as a yellow solid; EI-HRMS m/e calcd for $C_{18}H_{19}N_5OS$ ($M^+$) 353.1310, found 353.1307.

Example 41

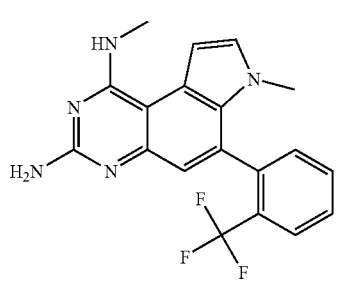

From 7-Methyl-6-(2-trifluoromethyl-phenyl)-7H-pyrrolo[3,2-f]quinazoline-1,3-diamine there was produced 7,N1-Dimethyl-6-(2-trifluoromethyl-phenyl)-7H-pyrrolo[3,2-f]quinazoline-1,3-diamine trifluoro-acetic acid salt; $^1$H NMR (DMSO-$d_6$, 400 MHz) δ 12.36 (m, 1H), 8.0 g (m, 1H), 7.98 (d, J=7.81 Hz, 1H), 7.81 (m, 3H), 7.71 (d, J=2.93 Hz, 1H), 7.61 (d, J=5.86 Hz, 1H), 7.41 (d, J=3.91 Hz, 1H), 7.04 (s, 1H), 3.21 (d, J=3.91 Hz, 3H), 3.17 (s, 3H).

Example 42

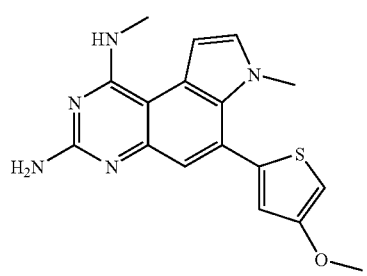

From 6-(4-Methoxy-thiophen-2-yl)-7-methyl-7H-pyrrolo[3,2-f]quinazoline-1,3-diamine there was produced 6-(4-Methoxy-thiophen-2-yl)-7,N1-dimethyl-7H-pyrrolo[3,2-f]quinazoline-1,3-diamine as a light yellow solid; EI-HRMS m/e calcd for $C_{17}H_{17}N_5OS$ ($M^+$) 339.1154, found 339.1148.

Example 42

In Vitro Inhibition of PTP1B

Enzymes

Human PTP1B (1-321) was cloned from a human cDNA library using conventional molecular biology techniques. The cDNA sequence was identical to the published human PTP1B sequence (Accession number M33689). The protein was expressed and purified from *E. coli* as described by Barford D. et. al J. Mol Biol (1994) 239, 726–730.

PTPase Assays

The measurement of PTPase activity was carried out using one of two methods:

The first method for the measurement of PTP1B inhibitory activity a tyrosine phosphorylated peptide based on the amino acid sequence of insulin receptor tyrosine autophosphorylation site 1146 (TRDI(pY)E) was used as substrate. The reaction conditions were as follows:

PTP1B (0.5–2 nM) was incubated with compound for 15 min in buffer containing 37.5 mM Bis-Tris buffer pH 6.2, 140 mMNaCl, 0.05% BSA and 2 mM DTT. The reaction was started by the addition of 50 μM substrate. After 20 min at room temperature (22–25° C.), the reaction was stopped with KOH and the amount of free phosphate measured using Malachite Green as previously described (Harder et al. 1994 Biochem J. 298; 395).

The second method was used for the measurement of general PTPase inhibitory activity across a panel of PTPases the substrate (6,8-difluoro-4-methylumbelliferyl phosphate (DiFMUP; from Molecular Probes) was used at the Km for each enzyme. The buffer conditions were identical as in the Malachite Green assay. The reaction was stopped with KOH. In this case the dephosphoryated product becomes fluorescent and the fluorescense read (Excitiation:360 mM/Emmission: 460 nM).

For kinetic experiments, the same buffer conditions were used except that the reaction was started using enzyme and the reaction stopped after 10 minutes.)

The IC50 values (in μM) for the PTP1B inhibitory activity of the compounds in the present application are in the range of 1.09 μM to 91.79 μM. The most preferred compounds show an IC50 of <30.0 μM.

Examples of some compounds with its corresponding IC50 values are

| Example | $IC_{50}$ (μM) |
| --- | --- |
| 2 | 7.10 |
| 4 | 9.47 |
| 6 | 10.22 |
| 8 | 11.35 |

Example 44

Glucose Uptake Assay

The day before the assay the SKMC media was changed to high glucose DMEM, 25 mM Hepes, pH 7.0 and 2% Charcoal/dextran treated FBS for 19 hours.

On the morning of the assay, cells were starved for max. 2 hours in low glucose (5.5 mM glucose) DMEM, 25 mM Hepes, pH 7.0 and 0.5% BSA. The starvation medium was removed and replaced with test medium (150 mMNaCl, 25 mM Hepes, pH 7.0) containing either 1% DMSO, or test compound diluted in DMSO or Porcine Insulin to a final concentrations of 1, 0.1, 0.05, 0.01 and 0.01 µM. Each assay point was performed in triplicate. The cells were incubated for 45 min at 37° C. 10 µM Cytochalasin B (CB) was added to appropriate wells to stop the active glucose transport (I.E., GLUT 1 & 4). At this point 2-Deoxy-D(U-$^{14}$C)glucose (Amersham, Code CFB195, 200 uCi/ml) was added to all wells to a final concentration of 0.8 µCi/ml. The cells were incubated for an additional 45 minutes at 37° C. in an incubator. Cells were then very gently washed for three times in PBS (RT). The cells were then lysed with the addition of 0.05% NaOH solution for 20 min at RT. The lysate was transferred to a scintillation vial containing 5 ml of scintillation fluid and counted in a Beckman LS6500 Scintillation counter. Analysis of results: The counts obtained with CB (passive glucose transport values) were subtracted from every value obtained with PI (or compounds) in order to evaluate only active glucose transport. Fold increase was calculated by dividing values in the presence of PI (or compounds) by the value obtained in the presence of DMSO (control). Compounds were considered to be active when they increase glucose uptake at least 25% of the Porcine Insulin response at 0.05 µM.

In vivo inhibition of PTP1B: Effects of compounds on blood glucose levels in mouse model To measure the anti-diabetic effect compounds were tested in well established rodent in vivo models of type 2 diabetes and obesity.

Example 45

Diet Induced Obese C57BL6/J Mice (DIO Mice)

Mice that have type 2 diabetes were generated by maintaining them on a high fat diet for 4–6 months (Diabetes vol. 37 September 1988). Male C57Bl6/J mice (age 3–4 weeks) were placed on high fat diet for 4–6 months. At this time they were hyperglycemic and hyperinsulinemic and weighed 40–50 g. DIO mice (n=10) were weighed and fasted for a two hour period prior to oral treatment. Immediately prior to dosing a pre-dose blood glucose reading was taken by snipping off a portion of the tail and collecting blood from the tail vein. Mice were treated either with a single dose of compound (acute) or once a day for 5 days (sub-chronic). For the acute studies, glucose was generally measured at 2 h, 4 h, 6 h, 8 h post treatment. Compounds were considered active if they showed a statistically significant (p≦0.05) glucose lowering (>15%) compared to the vehicle treated animals.

For sub-chronic (5 day) studies mice were dosed once a day by gavage as described above. On day five, glucose was measured prior to dosing (0time) and 2 hours after dosing. Insulin and triglycerides were measured at 2 hour post dose. Compounds were considered active if they showed a statistically significant (p<0.05) glucose, insulin and triglyceride lowering compared to the vehicle treated animals.

What is claimed is:
1. A compound of the formula:

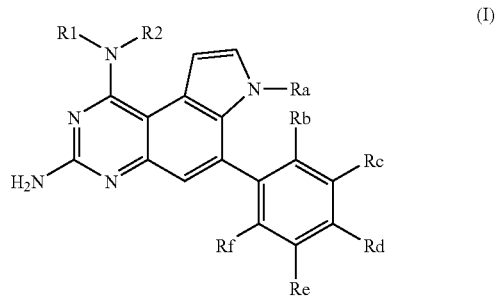

(I)

wherein,
R1 is selected from the group consisting of lower alkyl, aryl lower alkyl, acetyl, aryl lower alkoxy lower alkyl and mono- or di-hydroxy substituted lower alkyl;
R2 is selected from the group consisting of hydrogen, lower alkyl, aryl lower alkyl, acetyl, mono- or di-hydroxy substituted lower alkyl and aryl lower alkoxy lower alkyl;
Ra is selected from the group consisting of hydrogen, aryl lower alkyl, lower alkyl, lower alkoxy, mono- or di-hydroxy substituted lower alkyl and

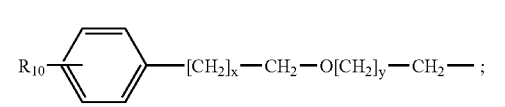

$R_{10}$ is selected from hydrogen and

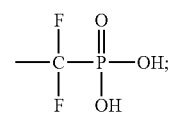

Rb, Rc, Rd, Re and Rf are individually selected from the group consisting of hydrogen, perfluro-lower alkyl, halogen, lower alkyl substituted aryl lower alkyl, lower alkoxy, aryl lower alkoxy and

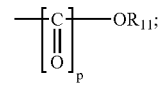

$R_{11}$ is selected from hydrogen, lower alkyl and aryl;
p is an integer from 0 to 1; and
x and y are individually integers from 0 to 4,
or a pharmaceutically acceptable salt thereof.
2. The compound of claim 1 wherein
R1 is selected from the group consisting of methyl, ethyl, benzyl, acetyl, 2,3-dihydroxypropyl, 3-hydroxypropyl and 2-benzyloxyethyl;
R2 is selected from the group consisting of hydrogen, methyl, ethyl, benzyl, and acetyl;
Ra is selected from the group consisting of hydrogen, methyl, hydroxyethyl, 2-benzyloxy-ethyl and 2-[4-difluorophosphono-methyl]-benzyloxy]-ethyl;

Rb is selected from the group consisting of hydrogen, methyl, methoxy, phenoxy and trifluoromethyl;

Rc and Rd are each independently selected from hydrogen and trifluoromethyl;

Re is selected from the group consisting of hydrogen, chlorine and trifluoromethyl; and Rf is selected from hydrogen and methyl.

3. A compound of the formula:

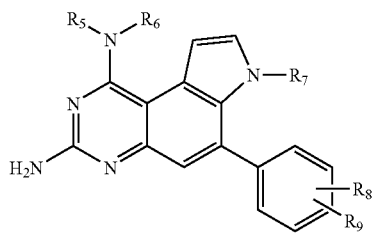

I-A wherein, $R_5$ is selected from the group consisting of hydrogen, lower alkyl, aryl lower alkyl, mono- or di-hydroxy substituted lower alkyl and aryl lower alkoxy loweralkyl;

$R_6$ is selected from the group consisting of lower alkyl, aryl lower alkyl, mono- or di-hydroxy substituted lower alkyl and aryl lower alkoxy lower alkyl;

$R_7$ is selected from the group consisting of hydrogen, lower alkyl, mono- or di-hydroxy substituted lower alkyl, and

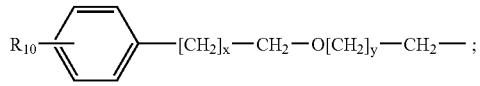

$R_{10}$ is selected from hydrogen and

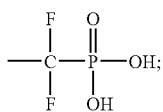

$R_8$ and $R_9$ are individually selected from the group consisting of hydrogen, perfluoro-lower alkyl, halogen, lower alkyl substituted aryl lower alkyl, lower alkyl, aryl lower alkoxy and

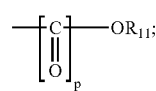

$R_{11}$ is selected from hydrogen, aryl and lower alkyl;

p is an integer from 0 to 1; and x and y are individually integers from 0 to 4, or a pharmaceutically acceptable salt thereof.

4. The compound of claim 3 wherein $R_5$ is selected from hydrogen and lower alkyl;

$R_6$ is lower alkyl; and $R_8$ and $R_9$ are selected from perfluoroloweralkyl and hydrogen with at least one or $R_8$ and $R_9$ being perfluoroloweralkyl.

5. The compound of claim 4 wherein $R_7$ is selected from hydrogen and lower alkyl.

6. The compound of claim 5 wherein said compound is 7,N1,N1-trimethyl-6-(2-trifluoromethyl-phenyl)-7H-pyrrolo[3,2-f]quinazoline-1,3-diamine trifluoro-acetic acid salt.

7. The compound of claim 5 wherein said compound is N1,N1-diethyl-7-methyl-6-(2-trifluoromethyl-phenyl)-7H-pyrrolo[3,2-f]quinazoline-1,3-diamine trifluoro-acetic acid salt.

8. The compound of claim 5 wherein said compound is 7-methyl-N1,N1-dipropyl-6-(2-trifluoromethyl-phenyl)-7H-pyrrolo[3,2-f]quinazoline-1,3-diamine trifluor-acetic acid salt.

9. The compound of claim 5 wherein said compound is 7,N1,N1-trimethyl-6-(4-trifluoromethyl-phenyl)-7H-pyrrolo[3,2-f]quinazoline-1,3-diamine.

10. The compound of claim 5 wherein said compound is 7,N1-dimethyl-6-(2-trifluoromethyl-phenyl)-7H-pyrrolo[3,2-f]quinazoline-1,3-diamine trifluoro-acetic acid salt.

11. The compound of claim 4 wherein $R_7$ is mono- or di-hydroxy substituted lower alkyl.

12. The compound of claim 11 wherein said compound is 2-[3-amino-1-dimethylamino-6-(2-trifluoromethyl-phenyl)-pyrrolo[3,2-f]quinazolin-7-yl]-ethanol trifluoro-acetic acid salt.

13. The compound of claim 3 wherein $R_5$ is hydrogen or mono- or di-hydroxy substituted lower alkyl, $R_6$ is mono- or di-hydroxy substituted lower alkyl, and $R_8$ and $R_9$ are independently selected from perfluoroloweralkyl and hydrogen with at least one of said $R_8$ and $R_9$ being perfluoroloweralkyl.

14. The compound of claim 13 wherein said compound is 3-[3-amino-7-methyl-6-(2-trifluoromethyl-phenyl)-7H-pyrrolo[3,2-f]quinazolin-1-ylamino]-propan-1-ol trifluoro-acetic acid salt.

15. The compound of claim 13 wherein said compound is 3-[3-amino-7-methyl-6-(2-trifluoromethyl-phenyl)-7H-pyrrolo[3,2-f]quinazolin-1-ylamino]-propane-1,2-diol trifluoro-acetic acid salt.

16. The compound of claim 13 wherein said compound is 2-[[3-amino-7-methyl-6-(2-trifluoromethyl-phenyl)-7H-pyrrolo[3,2-f]quinazolin-1-yl]-(2-hydroxy-ethyl)-amino]-ethanol trifluoro-acetic acid salt.

17. The compound of claim 4 wherein $R_7$ is

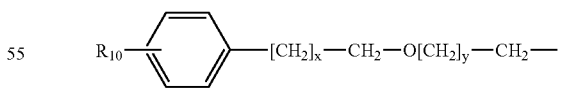

and $R_{10}$, x and y are as above.

18. The compound of claim 17 wherein said compound is [(4-{2-[3-amino-1-dimethylamino-6-(2-trifluoromethyl-phenyl)-pyrrolo[3,2-f]quinazolin-7-yl]-ethoxymethyl}-phenyl)-difluoro-methyl]-phosphonic acid.

19. The compound of claim 17 wherein said compound is produced 7,N1-bis-(2-benzyloxy-ethyl)-6-(2-trifluoromethyl-phenyl)-7H-pyrrolo[3,2-f]quinazoline-1,3-diamine trifluoro-acetic acid salt.

20. The compound of claim 3 wherein one of $R_8$ or $R_9$ is selected from

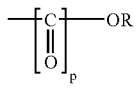

and lower alkoxy, and p is as above.

21. The compound of claim 20 wherein said compound is 6-(2-methoxy-phenyl)-7,N1-dimethyl-7H-pyrrolo[3,2-f]quinazoline-1,3-diamine trifluoro-acetic acid salt.

22. The compound of claim 20 wherein said compound is 6-(2-methoxy-phenyl)-7,N1,N1-trimethyl-7H-pyrrolo[3,2-f]quinazoline-1,3-diamine trifluoro-acetic acid salt.

23. The compound of claim 3 wherein one of $R_8$ and $R_9$ is lower alkyl.

24. The compound of claim 23 wherein said compound is 6-(2,6-dimethyl-phenyl)-7,N1,N1-trimethyl-7H-pyrrolo[3,2-f]quinazoline-1,3-diamine trifluoro-acetic acid salt.

25. The compound of the formula

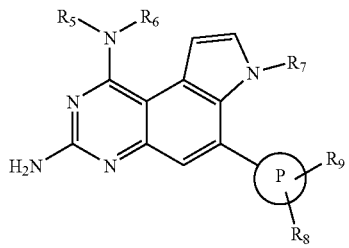

(I-B)

wherein,

Ⓟ is a 5 or 6 membered heteroaromatic ring containing from 1 to 2 hetero atoms selected from the group consisting of oxygen, sulfur and nitrogen;

$R_5$ is selected from the group consisting of hydrogen, lower alkyl, aryl lower alkyl, mono- or di-hydroxy substituted lower alkyl, and aryl lower alkoxy lower-alkyl;

$R_6$ is selected from the group consisting of lower alkyl, aryl lower alkyl, mono- or di-hydroxy substituted lower alkyl, and aryl lower alkoxy lower alkyl;

$R_7$ is selected from the group consisting of hydrogen, aryl lower alkyl, lower alkyl, lower alkoxy, mono- or di-hydroxy substituted lower alkyl, and

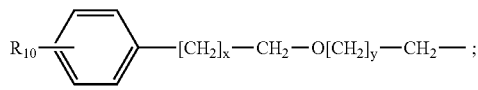

$R_{10}$ is selected from hydrogen and

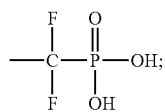

$R_8$ and $R_9$ are individually selected from the group consisting of hydrogen, perfluoro-lower alkyl, halogen, lower alkyl substituted aryl lower alkyl, lower alkyl, aryl lower alkoxy and

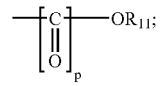

$R_{11}$ is selected from the group consisting of hydrogen, lower alkyl and aryl;

p is an integer from 0 to 1; and x and y are individually integers from 0 to 4, or a pharmaceutically acceptable salt thereof.

26. The compound of claim 25 wherein Ⓟ is a 5 or 6 membered heteroaromatic ring containing a sulfur hetero atoms as the only heteroaromatic atom in said ring.

27. The compound of claim 26 wherein $R_8$ and $R_9$ are selected from hydrogen and lower alkyl;

$R_5$ is selected from the group consisting of hydrogen, lower alkyl and mono- or di-hydroxy substituted lower alkyl; and $R_6$ is selected from lower alkyl and mono- or di-hydroxy substituted lower alkyl.

28. The compound of claim 27 wherein said compound is 2-(3-amino-7-methyl-6-thiophen-2-yl-7H-pyrrolo[3,2-f]quinazolin-1-ylamino)-ethanol trifluoro-acetic acid salt.

29. The compound of claim 27 wherein said compound is 2-[3-amino-7-methyl-6-(5-methyl-thiophen-2-yl)-7H-pyrrolo[3,2-f]quinazolin-1-ylamino]-ethanol trifluoro-acetic acid salt.

30. The compound of claim 27 wherein said compound is 3-(3-amino-7-methyl-6-thiophen-2-yl-7H-pyrrolo[3,2-f]quinazolin-1-ylamino)-propan-1-ol trifluoro-acetic acid salt.

31. The compound of claim 27 wherein said compound is 7,N1-dimethyl-6-thiophen-2-yl-7H-pyrrolo[3,2-f]quinazoline-1,3-diamine trifluoro-acetic acid salt.

32. The compound of claim 27 wherein said compound is 7,N1,N1-trimethyl-6-thiophen-2-yl-7H-pyrrolo[3,2-f]quinazoline-1,3-diamine.

33. The compound of claim 27 wherein said compound is 7,N1-dimethyl-6-(5-methyl-thiophen-2-yl)-7H-pyrrolo[3,2-f]quinazoline-1,3-diamine.

34. The compound of claim 27 wherein said compound is 7-ethyl-N1-methyl-6-thiophen-2-yl-7H-pyrrolo[3,2-f]quinazoline-1,3-diamine trifluoro-acetic acid salt.

35. The compound of claim 27 wherein said compound is 7-ethyl-N1,N1-dimethyl-6-thiophen-2-yl-7H-pyrrolo[3,2-f]quinazoline-1,3-diamine trifluoro-acetic acid salt.

36. The compound of claim 27 wherein said compound is N1,N1-diethyl-7-methyl-6-thiophen-2-yl-7H-pyrrolo[3,2-f]quinazoline-1,3-diamine trifluoro-acetic acid salt.

37. The compound of claim 26 wherein $R_8$ and $R_9$ are independently selected from the group consisting of hydrogen, lower alkoxy, and aryl lower alkoxy with at least one of $R_8$ and $R_9$ being other than hydrogen;

$R_5$ is selected from the group consisting of hydrogen, lower alkyl and mono- or di-hydroxy substituted lower alkyl; and $R_6$ is selected from lower alkyl and mono- or di-lower hydroxy substituted lower alkyl.

38. The compound of claim 37 wherein said compound is 6-(5-methoxy-thiophen-2-yl)-7,N1,N1-trimethyl-7H-pyrrolo[3,2-f]quinazoline-1,3-diamine.

39. The compound of claim 37 wherein said compound is 6-(5-methoxy-thiophen-2-yl)-7,N1-dimethyl-7H-pyrrolo[3,2-f]quinazoline-1,3-diamine.

40. The compound of claim 37 wherein said compound is 6-(4-methoxy-thiophen-2-yl)-7,N1,N1-trimethyl-7H-pyrrolo[3,2-f]quinazoline-1,3-diamine.

41. The compound of claim 37 wherein said compound is 6-(4-methoxy-thiophen-2-yl)-7,N1-dimethyl-7H-pyrrolo[3,2-f]quinazoline-1,3-diamine.

42. The compound of claim 25 wherein
Ⓟ is a 5 or 6 membered heteroaromatic ring containing an oxygen atom as the only hetero atom.

43. The compound of claim 42 wherein
$R_5$ is selected from hydrogen and lower alkyl; and
$R_6$ is lower alkyl.

44. The compound of claim 43 wherein said compound is 6-furan-3-yl-7,N1,N1-trimethyl-7H-pyrrolo[3,2-f]quinazoline-1,3-diamine.

45. The compound of claim 43 wherein said compound is 6-furan-2-yl-7,N1-dimethyl-7H-pyrrolo[3,2-f]quinazoline-1,3-diamine trifluoro-acetic acid salt.

46. The compound of claim 25 wherein Ⓟ is a 5 or 6 membered heteroaromatic ring containing a nitrogen atom as the only hetero atom.

47. The compound of claim 46 wherein
one of $R_8$ and $R_9$ is hydrogen and the other is selected from hydrogen, lower alkyl and $$-O-\underset{\underset{O}{\|}}{C}-OR_{11}$$

wherein
$R_{11}$ is selected from aryl and lower alkyl; and
$R_5$ and R6 are lower alkyl.

48. The compound of claim 47 wherein said compound is 2-(3-amino-1-dimethylamino-7-methyl-7H-pyrrolo[3,2-f]quinazolin-6-yl)-pyrrole-1-carboxylic acid tert-butyl ester.

49. The compound of claim 25 wherein Ⓟ is a 5 or 6 membered heteroaromatic ring containing two heteroatoms.

50. The compound of claim 49 wherein $R_8$ and $R_9$ are independently selected from the group consisting of lower alkyl, hydrogen and lower alkoxy.

51. The compound of claim 50 wherein said compound is 6-(2,4-dimethoxy-pyrimidin-5-yl)-7,N1,N1-trimethyl-7H-pyrrolo[3,2-f]quinazoline-1,3-diamine.

52. A pharmaceutical composition comprising one or more compounds of the formula:

(I)

wherein,
R1 is selected from the group consisting of lower alkyl, aryl lower alkyl, acetyl, aryl lower alkoxy lower alkyl, and mono- or di-hydroxy substituted lower alkyl;

R2 is selected from the group consisting of hydrogen, lower alkyl, aryl lower alkyl, acetyl, mono- or di-hydroxy substituted lower alkyl and aryl lower alkoxy lower alkyl;

Ra is selected from the group consisting of hydrogen, aryl lower alkyl, lower alkyl, lower alkoxy, mono- or di-hydroxy substituted lower alkyl and $$R_{10}-\underset{}{\bigcirc}-[CH_2]_x-CH_2-O[CH_2]_y-CH_2-\ ;$$

$R_{10}$ is selected from hydrogen and $$-\underset{\underset{F}{|}}{\overset{F}{\underset{|}{C}}}-\underset{\underset{OH}{\|}}{\overset{O}{P}}-OH;$$

$R_8$ and $R_9$ are individually selected from the group consisting of hydrogen, perfluoro-lower alkyl, halogen, lower alkyl substituted aryl lower alkyl, lower alkyl, aryl lower alkoxy and $$-\left[\underset{\underset{O}{\|}}{C}\right]_p-OR_{11};$$

$R_{11}$ is selected from hydrogen, lower alkyl and aryl;
p is an integer from 0 to 1; and
x and y are individually integers from 0 to 4,
or a pharmaceutically acceptable salt thereof.

53. A pharmaceutical composition comprising one or more compounds of the formula:

I-A wherein,
$R_5$ is selected from the group consisting of hydrogen, lower alkyl, aryl lower alkyl, mono- or di-hydroxy substituted lower alkyl, and aryl lower alkoxy lower-alkyl;

$R_6$ is lower alkyl, aryl lower alkyl, mono- or di-hydroxy substituted lower alkyl, and aryl lower alkoxy lower alkyl;

$R_7$ is hydrogen, lower alkyl, mono- or di-hydroxy substituted lower alkyl, and

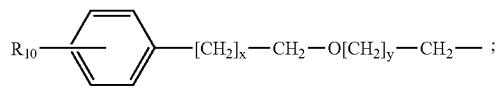

$R_{10}$ is selected from hydrogen and

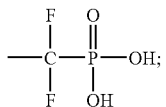

$R_8$ and $R_9$ are individually selected from the group consisting of hydrogen, perfluoro-lower alkyl, halogen, lower alkyl substituted aryl lower alkyl, lower alkyl, aryl lower alkoxy, phenoxy, and

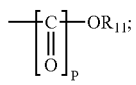

$R_{11}$, is selected from hydrogen, aryl and lower alkyl;
p is an integer from 0 to 1; and
x and y are individually integers from 0 to 4,
or a pharmaceutically acceptable salt thereof.

54. A method of treating diabetes comprising administering to a patient in need of such treatment a therapeutically effective amount of at least one compound of the formula:

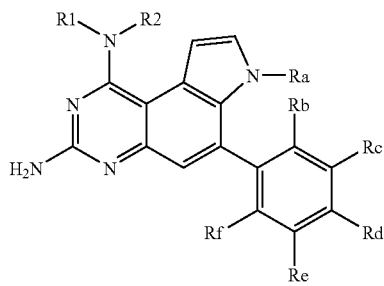

(I)

wherein,
R1 is selected from the group consisting of lower alkyl, aryl lower alkyl; acetyl, aryl lower alkoxy lower alkyl, and mono- or di-hydroxy substituted lower alkyl;
R2 is selected from the group consisting of hydrogen, lower alkyl, aryl lower alkyl, acetyl, mono- or di-hydroxy substituted lower alkyl, and aryl lower alkoxy lower alkyl;
Ra is selected from the group consisting of hydrogen, aryl lower alkyl, lower alkyl, lower alkoxy, mono- or di-hydroxy substituted lower alkyl and

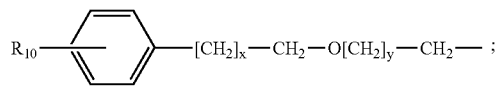

$R_{10}$ is selected from hydrogen and

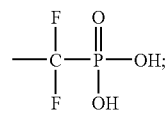

Rb, Rc, Rd, Re and Rf are individually selected from the group consisting of hydrogen, perfluro-lower alkyl, halogen, lower alkyl substituted aryl lower alkyl, lower alkoxy, aryl lower alkoxy and $$-\left[\underset{\underset{O}{\overset{\|}{C}}}{}\right]_p-OR_{11};$$

$R_{11}$ is selected from hydrogen, lower alkyl and aryl;
p is an integer from 0 to 1; and
x and y are individually integers from 0 to 4,
or a pharmaceutically acceptable salt thereof.

55. A method of treating diabetes comprising administering to a patient in need of such treatment a therapeutically effective amount of at least one compound of the formula:

I-A

[Structure with $R_5$, $R_6$, $R_7$, $H_2N$, $R_8$, $R_9$]

wherein,
$R_5$ is selected from the group consisting of hydrogen, lower alkyl, aryl lower alkyl, mono- or di-hydroxy substituted lower alkyl, and aryl lower alkoxy lower-alkyl;
$R_6$ is selected from the group consisting of lower alkyl, aryl lower alkyl, mono- or di-hydroxy substituted lower alkyl, and aryl lower alkoxy lower alkyl;
$R_7$ is hydrogen, lower alkyl, mono- or di-hydroxy substituted lower alkyl, and

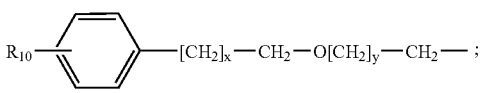

$R_{10}$ is selected from hydrogen and $$-\underset{\underset{F}{\overset{F}{|}}}{C}-\underset{\underset{OH}{\overset{O}{\|}}}{P}-OH;$$

$R_8$ and $R_9$ are individually selected from the group consisting of hydrogen, perfluoro-lower alkyl, halogen, lower alkyl substituted aryl lower alkyl, lower alkyl, aryl lower alkoxy, phenoxy and

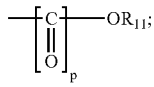

$R_{11}$ is selected from hydrogen, aryl and lower alkyl;

p is an integer from 0 to 1; and x and y are individually integers from 0 to 4, or a pharmaceutically acceptable salt thereof.

56. A pharmaceutical composition comprising one or more compounds of the formula:

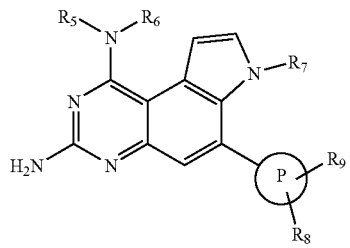

(I-B)

wherein,

- Ⓟ is a 5 or 6 membered heteroaromatic ring containing from 1 to 2 hetero atoms selected from the group consisting of oxygen, sulfur and nitrogen;
- $R_5$ is selected from the group consisting of hydrogen, lower alkyl, aryl lower alkyl, mono- or di-hydroxy substituted lower alkyl, and aryl lower alkoxy lower-alkyl;
- $R_6$ is selected from the group consisting of lower alkyl, aryl lower alkyl, mono- or di-hydroxy substituted lower alkyl, and aryl lower alkoxy lower alkyl;
- $R_7$ is selected from the group consisting of hydrogen, aryl lower alkyl, lower alkyl, lower alkoxy, mono- or di-hydroxy substituted lower alkyl and

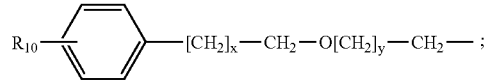

$R_{10}$ is selected from hydrogen and

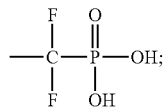

$R_8$ and $R_9$ are individually selected from the group consisting of hydrogen, perfluoro-lower alkyl, halogen, lower alkyl substituted aryl lower alkyl, lower alkyl, aryl lower alkoxy and

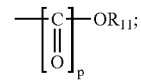

$R_{11}$ is selected from the group consisting of hydrogen, lower alkyl and aryl;

p is an integer from 0 to 1; and x and y are individually integers from 0 to 4, or a pharmaceutically acceptable salt thereof.

57. A method of treating diabetes comprising administering to a patient in need of such treatment a therapeutically effective amount of at least one compound of the formula:

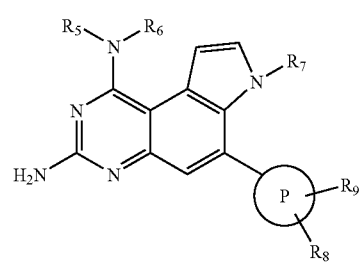

(I-B)

wherein,

- Ⓟ is a 5 or 6 membered heteroaromatic ring containing from 1 to 2 hetero atoms selected from the group consisting of oxygen, sulfur and nitrogen;
- $R_5$ is selected from the group consisting of hydrogen, lower alkyl, aryl lower alkyl, mono- or di-hydroxy substituted lower alkyl, and aryl lower alkoxy lower-alkyl;
- $R_6$ is selected from the group consisting of lower alkyl, aryl lower alkyl, mono- or di-hydroxy substituted lower alkyl, and aryl lower alkoxy lower alkyl;
- $R_7$ is selected from the group consisting of hydrogen, aryl lower alkyl, lower alkyl, lower alkoxy, mono- or di-hydroxy substituted lower alkyl and

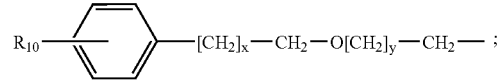

$R_{10}$ is selected from hydrogen and

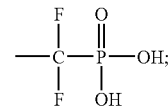

$R_8$ and $R_9$ are individually selected from the group consisting of hydrogen, perfluoro-lower alkyl, halogen, lower alkyl substituted aryl lower alkyl, lower alkyl, aryl lower alkoxy and

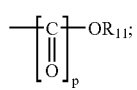
$R_{11}$ is selected from the group consisting of hydrogen, lower alkyl and aryl;
p is an integer from 0 to 1; and
x and y are individually integers from 0 to 4
or a pharmaceutically acceptable salt thereof.
* * * * *